(12) United States Patent
Siomina et al.

(10) Patent No.: US 9,722,744 B2
(45) Date of Patent: Aug. 1, 2017

(54) DETERMINING SIGNAL TRANSMISSION BANDWIDTH

(71) Applicant: Telefonaktiebolaget L M Ericsson (publ), Stockholm (SE)

(72) Inventors: Iana Siomina, Täby (SE); Muhammad Kazmi, Bromma (SE); Bengt Lindoff, Bjärred (SE)

(73) Assignee: Telefonaktiebolaget LM Ericsson (publ), Stockholm (SE)

(*) Notice: Subject to any disclaimer, the term of this patent is extended or adjusted under 35 U.S.C. 154(b) by 75 days.

(21) Appl. No.: 14/760,523

(22) PCT Filed: Oct. 28, 2013

(86) PCT No.: PCT/SE2013/051255
§ 371 (c)(1),
(2) Date: Jul. 13, 2015

(87) PCT Pub. No.: WO2014/112916
PCT Pub. Date: Jul. 24, 2014

(65) Prior Publication Data
US 2015/0358131 A1    Dec. 10, 2015

Related U.S. Application Data

(60) Provisional application No. 61/753,511, filed on Jan. 17, 2013.

(51) Int. Cl.
*H04L 5/00* (2006.01)
*H04J 11/00* (2006.01)
(Continued)

(52) U.S. Cl.
CPC ............ *H04L 5/0032* (2013.01); *A61K 38/39* (2013.01); *H04J 11/0056* (2013.01);
(Continued)

(58) Field of Classification Search
CPC .......... H04J 11/00; H04L 27/26; H04W 72/08
See application file for complete search history.

(56) References Cited

U.S. PATENT DOCUMENTS

2007/0140106 A1*  6/2007  Tsai ..................... H04B 7/2681
370/208
2009/0181669 A1*  7/2009  Naka .................... H04L 5/0007
455/434
(Continued)

FOREIGN PATENT DOCUMENTS

EP    1860785 A2   11/2007
EP    2020770 A1    2/2009
(Continued)

*Primary Examiner* — Jamal Javaid
*Assistant Examiner* — Kyaw Z Soe
(74) *Attorney, Agent, or Firm* — Murphy, Bilak & Homiller, PLLC

(57) ABSTRACT

Example embodiments presented herein are directed towards a first radio node (400), and corresponding methods therein, for determining a bandwidth of a second radio node (402). The first and second radio nodes are configured for use in a communications network. The bandwidth is determined based on a correlation between a signal received form the second radio node and at least one known signal which are transmittable on one or more known radio resources. Such bandwidth determination eliminates the need for the wireless terminal to receive such information via system information broadcasted from a cell.

23 Claims, 11 Drawing Sheets

(51) Int. Cl.
*H04L 27/26* (2006.01)
*H04W 72/08* (2009.01)
*A61K 38/39* (2006.01)

(52) U.S. Cl.
CPC .......... *H04J 11/0079* (2013.01); *H04L 5/005* (2013.01); *H04L 5/0007* (2013.01); *H04L 5/0051* (2013.01); *H04L 27/2659* (2013.01); *H04W 72/085* (2013.01); *H04J 2011/0096* (2013.01)

(56) References Cited

U.S. PATENT DOCUMENTS

| | | | |
|---|---|---|---|
| 2012/0008576 A1* | 1/2012 | Lin | H04B 7/0691 370/329 |
| 2012/0046047 A1* | 2/2012 | Popovic | G01S 5/0226 455/456.1 |
| 2012/0327797 A1 | 12/2012 | Siomina et al. | |
| 2014/0200001 A1* | 7/2014 | Song | H04W 36/0094 455/436 |
| 2014/0321314 A1* | 10/2014 | Fodor | H04W 72/085 370/252 |

FOREIGN PATENT DOCUMENTS

| | | |
|---|---|---|
| EP | 2207369 A1 | 7/2010 |
| JP | 2007060116 A | 3/2007 |
| WO | 2010093028 A1 | 8/2010 |

* cited by examiner

DETERMINING SIGNAL TRANSMISSION BANDWIDTH

TECHNICAL FIELD

Example embodiments presented herein are directed towards a first radio node, and corresponding methods therein, for determining a bandwidth of a second radio node in a communications network.

BACKGROUND

Communications Network Overview

In a typical cellular system, also referred to as a wireless communications network, wireless terminals or wireless devices, also known as mobile stations and/or user equipments (UEs) communicate via a Radio Access Network (RAN) to one or more core networks. The wireless terminals can be mobile stations or user equipment units such as mobile telephones also known as "cellular" telephones, and laptops with wireless capability, e.g., mobile termination, and thus can be, for example, portable, pocket, hand-held, computer-comprised, or car-mounted mobile devices which communicate voice and/or data with radio access network.

The radio access network covers a geographical area which is divided into cell areas, with each cell area being served by a base station, e.g., a Radio Base Station (RBS), which in some networks is also called "NodeB" or "B node" and which in this document also is referred to as a base station. A cell is a geographical area where radio coverage is provided by the radio base station equipment at a base station site. Each cell is identified by an identity within the local radio area, which is broadcast in the cell. The base stations communicate over the air interface operating on radio frequencies with the user equipment units within range of the base stations.

In some versions of the radio access network, several base stations are typically connected, e.g., by landlines or microwave, to a Radio Network Controller (RNC). The radio network controller, also sometimes termed a Base Station Controller (BSC), supervises and coordinates various activities of the plural base stations connected thereto. The radio network controllers are typically connected to one or more core networks.

The Universal Mobile Telecommunications System (UMTS) is a third generation mobile communication system, which evolved from the Global System for Mobile Communications (GSM), and is intended to provide improved mobile communication services based on Wideband Code Division Multiple Access (WCDMA) access technology. UMTS Terrestrial Radio Access Network (UTRAN) is essentially a radio access network using wideband code division multiple access for user equipment units (UEs). The Third Generation Partnership Project (3GPP) has undertaken to evolve further the UTRAN and GSM based radio access network technologies. Long Term Evaluation (LTE) together with Evolved Packet Core (EPC) is the newest addition to the 3GPP family.

During operations, a user equipment will obtain bandwidth information from system information broadcast by a cell. The bandwidth information is a key parameter used for many purposes. Bandwidth information and the process for obtaining such information are described in greater detail below.

Bandwidth Information

In a cellular network a user equipment performs intra-frequency, inter-frequency, and/or inter-RAT measurements. FIG. 1A illustrates example intra-frequency scenarios. In all these scenarios the center frequency of the "target cell" and of the "current cell" are the same. However their bandwidth may or may not be the same. Furthermore the "target cell" is a measured cell, and a "current cell" is a serving cell (multiple serving cells may be utilized with carrier aggregation, for example, one PCell and one or more SCells). FIG. 1B illustrates example inter-frequency scenarios, where a "target cell" is a measured cell, and a "current cell" is a serving cell (multiple serving cells may be utilized with carrier aggregation, e.g., one PCell and one or more SCells). The target cell may be of the same or different RAT, which would result in an inter-RAT measurement. The bandwidth may be UL or DL bandwidth, which may or may not be the same. However in all the inter-frequency scenarios the center frequency of the "target cell" and of the "current cell" is not the same, for example, their center frequencies are shifted in the frequency domain.

In LTE, different bandwidth definitions exist. One example bandwidth definition in LTE is channel bandwidth. Channel bandwidth is the RF bandwidth supporting a single E-UTRA RF carrier with the transmission bandwidth configured in the uplink or downlink of a cell. The channel bandwidth is measured in MHz and is used as a reference for transmitter and receiver RF requirements.

A further example is a transmission bandwidth which is the bandwidth of an instantaneous transmission from a user equipment or BS, measured in Resource Block units. Yet another example is a transmission bandwidth configuration which is the highest transmission bandwidth allowed for uplink or downlink in a given channel bandwidth, measured in Resource Block units.

Another example is an aggregated channel bandwidth which is the RF bandwidth in which a base station or user equipment transmits and receives multiple contiguously aggregated carriers. The aggregated channel bandwidth is measured in MHz. Yet a further example is a subblock bandwidth which is the bandwidth of one subblock, where the subblock is one contiguous allocated block of spectrum for transmission and reception by the same base station or user equipment. There may be multiple instances of subblocks within an RF bandwidth. A further example is a measurement bandwidth which is the bandwidth over which a measurement is performed. The measurement bandwidth of a signal cannot exceed its transmission bandwidth.

Examples of such bandwidths are provided in the figures. FIG. 2A illustrates a channel bandwidth and transmission bandwidth configuration for an E-UTRA carrier. FIG. 2B illustrates an aggregated channel bandwidth for an intra-band carrier aggregation. FIG. 2C illustrates a sub-block bandwidth for an intra-band non-contiguous spectrum.

The bandwidth information is one of the key parameters used for many purposes, for example, for adapting receiver configuration for performing a measurement. Normally, the bandwidth information is read from system information broadcasted by the cell, for example, from MIB transmitted via PBCH.

System Information

In LTE, the system information is divided into the MasterInformationBlock (MIB) and a number of SystemInformationBlocks (SIBs). MIB defines the most essential physical layer information of the cell required to receive further system information. MIB comprises parameters such as dl-Bandwidth, phich-Config, and systemFrameNumber.

The MIB is mapped on the BCCH and carried on BCH while all other SI messages are mapped on the BCCH and dynamically carried on DL-SCH where they may be identified through the SI-RNTI (System Information RNTI). MIB is transmitted according to a fixed schedule with a periodicity of 40 ms in subframes #0. To improve MIB detection performance, 3 redundancy versions are also signaled with 10 ms period.

SystemInformationBlockType1 comprises information relevant when evaluating if a user equipment is allowed to access a cell and defines the scheduling of other system information blocks, including SIB2. SIB1 may be broadcasted or transmitted in dedicated signaling in a RRCConnectionReconfiguration message at HO or for inter-cell interference purpose. UL bandwidth (if different from DL bandwidth) may be transmitted in SIB2.

SUMMARY

As described above, normally, a user equipment reads the cell bandwidth information from system information broadcasted by the cell. However, there are scenarios when this information cannot be obtained via system information or when such methods are not efficient. Thus, at least one example object of the example embodiments presented herein is to provide alternative methods for obtaining cell bandwidth information.

Providing alternative methods for obtaining cell bandwidth information, according to the example embodiments presented herein, provide various advantages. At least one example advantage is the possibility of avoiding the need for reading system information and additional higher-signaling, by means of obtaining the bandwidth information autonomously.

A further example advantage is the ability to improve receiver performance with the obtained bandwidth. The improvement of the receive performance is done with reduced complexity as the reading of system information may be avoided. Yet a further example advantage is the possibility to enable new carrier types without PBCH transmissions to increase spectrum efficiency and reduce energy consumption in the base station. Another example advantage is that the example embodiments provide the possibility for a network node to collect the bandwidth information of neighbor radio nodes from wireless devices.

Accordingly, some of the example embodiments are directed towards a method, in a first radio node, for determining a bandwidth of a second radio node. The first and second radio nodes are configured for use in a communications network. The method comprises receiving, from the second radio node, a radio signal. The method also comprises determining at least one known signal, where the at least one known signal is transmittable on one or more known radio resources. Examples of radio resources are one or more of resource elements, resource blocks, time slots, subframe, radio frame, carrier frequency, subcarrier, channel bandwidth or its part, channelization code, CDMA codes, etc. The method also comprises calculating a correlation between the radio signal and the at least one known signal. The method further comprises determining a bandwidth of the second radio node based on the calculating.

Some of the example embodiments are directed towards a first radio node for determining a bandwidth of a second radio node. The first and second radio nodes are configured for use in a communications network. The first radio node comprises radio circuitry configured to receive, from the second radio node, a radio signal. The first radio node further comprises processing circuitry configured to determine at least one known signal, where the at least one known signal being transmittable on one or more known resource elements. The processing circuitry is further configured to calculate a correlation between the radio signal and the at least one known signal. The processing circuitry is also configured to determine a bandwidth of the second radio node based on the calculated correlation.

DEFINITIONS

3GPP 3rd Generation Partnership Project
ADC Analog to Digital Converter
BCCH Broadcast Control Channel
BCH Broadcast Channel
BS Base Station
BW Bandwidth
CA Carrier Aggregation
CP Cyclic Prefix
CRS Cell-specific Reference Signal
CSG Closed Subscriber Group
CSI Channel State Information
DAC Digital to Analog Converter
DC Dual Carrier
DL Downlink
DM DeModulation
DRX Discontinuous Reception
eICIC enhanced ICIC
eNodeB evolved Node B
E-SMLC Evolved SMLC
FeICIC Further enhanced ICIC
GSM Global System for Mobile communications
HO Handover
HSPA High-Speed Packet Access
IC Interference Cancellation
ICIC Inter-cell Interference Coordination
LTE Long-Term Evolution
LMU Location Measurement Unit
MDT Minimization of Drive Tests
MIB Master Information Block
MME Mobility Management Entity
MSR Multi Standard Radio
O&M Operation and Maintenance
OFDM Orthogonal Frequency Division Multiplex
PBCH Physical Broadcast CHannel
PCC Policy Control and Charging
PCell Primary Cell
PCI Physical Cell Identity
PDN Packet Data Network
PGW PDN Gateway
PLMN Public Land Mobile Network
PRS Positioning Reference Signals
PSAP Public Safety Answering Point
PSS Primary Synchronization Signal
RAN Radio Access Network
RAT Radio Access Type
RB Resource Block
RE Resource Elements
RF Radio Frequency
RLM Radio Link Monitoring
RNC Radio network controller
RNTI Radio Network Temporary Identifier
RRC Radio Resource Control
RRH Remote Radio Head
RRM Radio Resource Management
RRU Remote Radio Unit
RS Reference Signal
RSRP Reference Signal Received Power
RSRQ Reference Signal Received Quality
RSSI Received Signal Strength Indicator RSTD Reference Signal Time Difference
Rx Receive
SCell Secondary Cell
SCC Secondary Component Carrier
SCG Service Continuity Gateway
SGW Serving Gateway
SI System Information
SIB System Information Block
SINR Signal-to-Interference Ratio
SON Self-Optimized Network
SRS Sounding Reference Signals
SSS Secondary Synchronization Signal
TDD Time Division Duplex
Tx Transmit
UE User Equipment
UL Uplink
UMTS Universal Mobile Telecommunications System

BRIEF DESCRIPTION OF THE DRAWINGS

The foregoing will be apparent from the following more particular description of the example embodiments, as illustrated in the accompanying drawings in which like reference characters refer to the same parts throughout the different views. The drawings are not necessarily to scale, emphasis instead being placed upon illustrating the example embodiments.

DETAILED DESCRIPTION

Figure 1A:
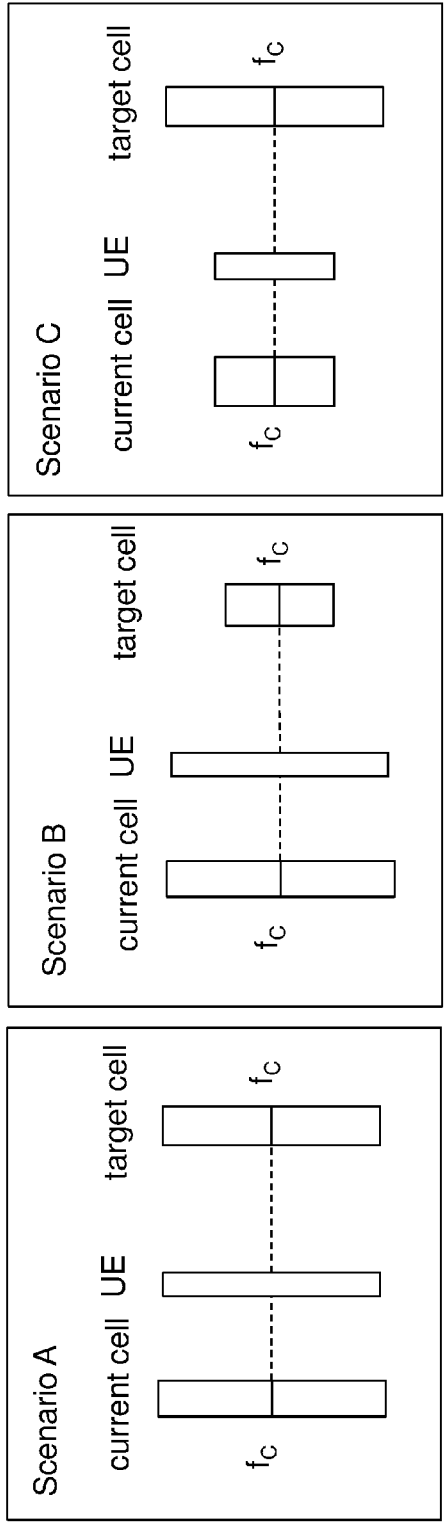
FIGS. 1A and 1B illustrate intra-frequency and inter-frequency, respectively, scenarios where a target cell is a measured cell and a current cell is a serving cell.

In the following description, for purposes of explanation and not limitation, specific details are set forth, such as particular components, elements, techniques, etc. in order to provide a thorough understanding of the example embodiments. However, it will be apparent to one skilled in the art that the example embodiments may be practiced in other manners that depart from these specific details. In other instances, detailed descriptions of well-known methods and elements are omitted so as not to obscure the description of the example embodiments. Various terminologies are utilized herein to describe the example embodiments. Definitions of such terminology are provided below.

A radio node is characterized by its ability to transmit and/or receive radio signals and it comprises at least a transmitting or receiving antenna. A radio node may be a wireless device, user equipment or a radio network node (see corresponding descriptions).

A wireless device, wireless terminal and user equipment are used interchangeably in the description. A user equipment may comprise any device equipped with a radio interface and capable of at least transmitting or receiving a radio signal from another radio node. A user equipment may also be capable of receiving signal and demodulate it. Note that even some radio network nodes, for example, femto BS (aka home BS), may also be equipped with a user equipment-like interface. Some examples of "UE" that are to be understood in a general sense are PDA, laptop, mobile, a tablet device, sensor, fixed relay, mobile relay, any radio network node equipped with a user equipment-like interface (e.g., small RBS, eNodeB, femto BS).

A radio network node is a radio node comprised in a radio communications network. A radio network node may be capable of receiving radio signals or transmitting radio signals in one or more frequencies, and may operate in single-RAT, multi-RAT or multi-standard mode (MSR). A radio network node, for example comprising eNodeB, RRH, RRU, or transmitting-only/receiving-only radio network nodes, may or may not create own cell. Some examples of radio network nodes not creating own cell are beacon devices transmitting configured radio signals or measuring nodes receiving and performing measurements on certain signals, for example, LMUs. It may also share a cell or the used cell ID with another radio node which creates own cell, it may operate in a cell sector or may be associated with a radio network node creating own cell. More than one cell or cell sectors (commonly named in the described embodiments by a generalized term "cell" which may be understood as a cell or its logical or geographical part) may be associated with one radio network node. Further, one or more serving cells (in DL and/or UL) may be configured for a user equipment, e.g., in a carrier aggregation system where a user equipment may have one Primary Cell (PCell) and one or more Secondary Cells (SCells). A cell may also be a virtual cell (e.g., characterized by a cell ID but not provide a full cell-like service) associated with a transmit node.

A network node may be any radio network node (see the corresponding description) or core network node. Some non-limiting examples of a network node are an eNodeB (also radio network node), RNC, positioning node, MME, PSAP, SON node, MDT node, coordinating node, a gateway node (e.g., P-GW or S-GW or LMU gateway or femto gateway), and O&M node.

The term "coordinating node" used herein is a network and/or node, which coordinates radio resources with one or more radio nodes. Some examples of the coordinating node are network monitoring and configuration node, OSS node, O&M, MDT node, SON node, positioning node, MME, a gateway node such as Packet Data Network Gateway (P-GW) or Serving Gateway (S-GW) network node or femto gateway node, a macro node coordinating smaller radio nodes associated with it, eNodeB coordinating resources with other eNodeBs, etc.

The signaling described in the example embodiments is either via direct links or logical links (e.g. via higher layer protocols and/or via one or more network and/or radio nodes). For example, signaling from a coordinating node to a user equipment may also pass another network node, e.g., a radio network node.

The described embodiments are not limited to LTE, but may apply with any Radio Access Network (RAN), single- or multi-RAT. Some other RAT examples are LTE-Advanced, UMTS, HSPA, GSM, cdma2000, WiMAX, and WiFi.

The example embodiments also apply to multi-point transmission and/or reception systems, carrier aggregation systems, and multi-point carrier aggregation systems.

The term "subframe" used in the embodiments described herein (typically related to LTE) is an example resource in the time domain, and in general it may be any pre-defined time instance or time period.

Enhanced receiver is a receiver implementing any of the embodiments described herein or implementing a receiver interference handling technique (e.g., interference cancellation, interference suppression, interference rejection, etc.). In some embodiments, "receiver type" may be used interchangeably with "receiver technique".

The term "victim" may apply e.g. to a measured signal or a measured cell (depending on the context), the measurements of which are performed in high-interference conditions.

The term "aggressor" may apply e.g. to a strongly interfering signal/channel or a strongly interfering radio node (e.g., a wireless device or a radio network node) or antenna or a cell (depending on the context), which interferers to the victim signal/channel/node/antenna/cell. In a cellular network, the interference may be e.g. intra-cell or inter-cell but may also be from device-to-device communication. The aggressor signal may be transmitted by the same node or a different node than that transmitting the victim signal (e.g., a cell of the same eNodeB or a cell of a different eNodeB; an intra-cell interfering signal is transmitted in the same cell by a different UE or by the same eNodeB using a different signal characteristic).

Some examples of victim-aggressor relations: an LTE physical signal to an LTE physical signal (of the same or different type) or to an LTE physical channel, an LTE physical channel to an LTE physical channel (of the same or different type) or an LTE physical signal, a macro cell or its user equipment interfering to a pico cell or the pico user equipment, a femto cell or a CSG user equipment interfering to a non-CSG cell or non-SCG user equipment, etc.

Overview of the Example Embodiments

In order to provide a better overview of the example embodiments, problems will first be identified and discussed. Normally, a user equipment reads cell bandwidth information from system information broadcasted by the cell. At least the following example problems may be envisioned with current methods of bandwidth determination.

First, the Physical Broadcast Channel (PBCH) is transmitted in every subframe #0 (every 10 ms) over 72 center subcarriers in the first four symbols of slot #1, for example, occupying almost 3% of REs of 1.4 MHz channel with normal CP. It is through the use of the PBCH that a user equipment may obtain cell bandwidth information. However, not transmitting PBCH (e.g., with a new carrier type) and obtaining this information (including the bandwidth) by other means may potentially increase spectrum utilization and make radio resource utilization more efficient, as is provided by the example embodiments presented herein.

A second example problem is that PBCH transmissions cause inter-cell interference which may be very severe in some scenarios, for example, in heterogeneous deployments with cell range extension when radio frame boundaries of the aggressor cell and measured cell are aligned. Obtaining PBCH of the measured (victim) cell may require a special receiver capability for mitigating the strong interference from aggressor PBCH, for example, PBCH interference cancellation may be needed. Not all user equipments may have such capability.

A third example problem is that some measurements, for example RSRP and RSRQ, may be performed on only 6 RBs. However, other measurements, for example, wideband RSRQ, UE Rx-Tx, RSTD, RLM, channel state measurements, etc., may need or have to be performed over a larger bandwidth when possible. Performance over a larger bandwidth may be needed when a larger channel bandwidth is used in the measured cell to improve measurement and/or system performance. Thus, a need exists for efficient and dynamic bandwidth determination in order to adapt a measurement bandwidth accordingly.

Figure 3:
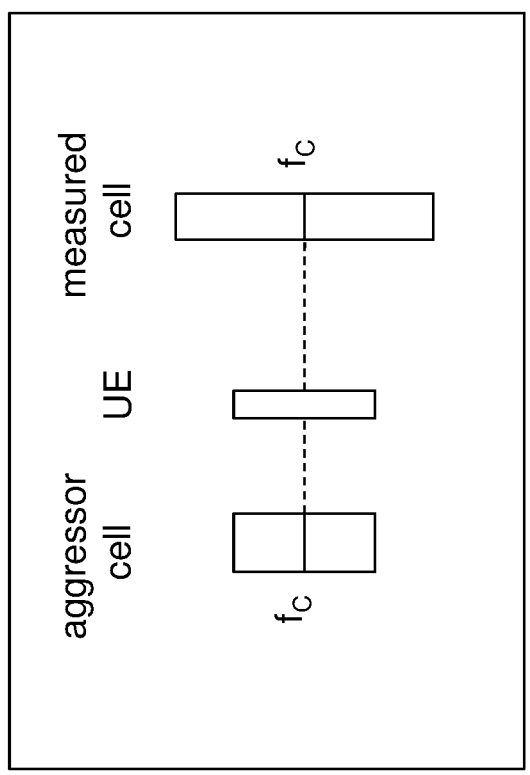
FIG. 3 is an illustrative example of bandwidths of an aggressor cell, user equipment and measured cell.

A fourth example problem is related to enhanced receivers. For enhanced receivers, it may be beneficial to know the bandwidth of the aggressor cell. For example, a receiver cancelling interference from aggressor CRS (e.g., to enhance RRM, RLM, CSI, or positioning measurements) would need to know the bandwidth over which the aggressor CRS are transmitted, as illustrated in FIG. 3, wherein the bandwidth of the aggressor cell is smaller than the bandwidth of the measured cell.

Figure 4:
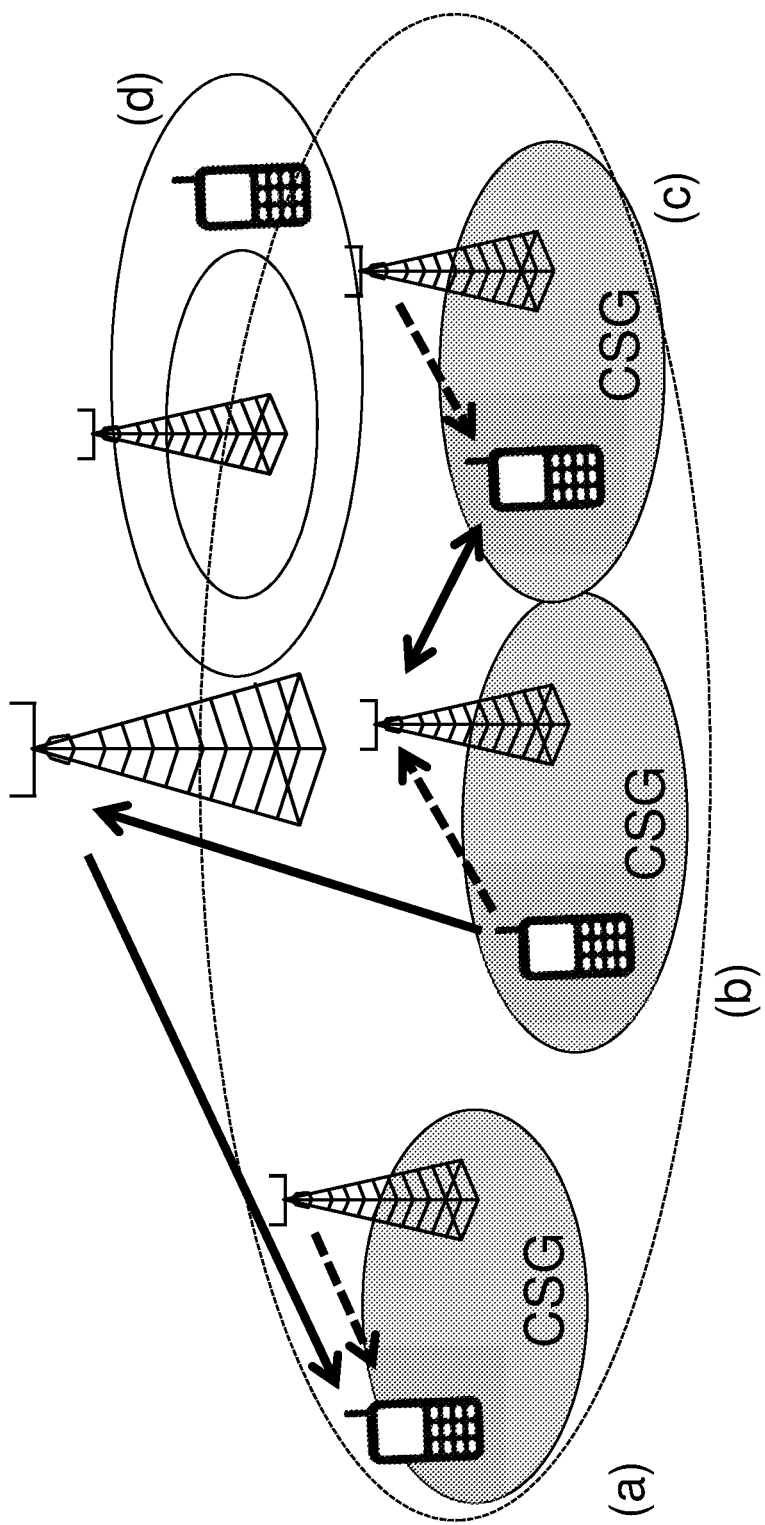
FIG. 4 is an illustrative example depicting various interference scenarios in heterogeneous deployments.

Some of the example embodiments presented herein may comprise signaling of the bandwidth information of a neighbor cell. However, the problem may exist already (e.g., in heterogeneous deployments) in releases when new signaling is not possible. Or the serving node may be not aware of the bandwidth of the neighboring interferer, for example, when the interfering node is another wireless device (e.g., in device-to-device communication), or when the interfering node is a CSG femto cell (the communication between home eNodeBs and e.g. macro eNodeBs is limited) or a user-deployed access point (in FIG. 4, in case (a), a macro user with no access to the Closed Subscriber Group (CSG) cell will be interfered by the home eNodeB, in case (b) a macro user causes severe interference towards the home eNodeB, in case (c) a CSG user is interfered by another CSG home eNodeB, and in case (d) a UE is served by a pico cell in the expended cell range area).

Above, the importance of bandwidth information and example problems related to obtaining bandwidth information has been provided. While bandwidth information is typically obtained from system information broadcasts, there are scenarios when this information cannot be obtained in this way, therefore alternative methods are necessary. Furthermore, the need for interference management or cancellation also provides a need for efficient and dynamic bandwidth determination.

Figure 5:
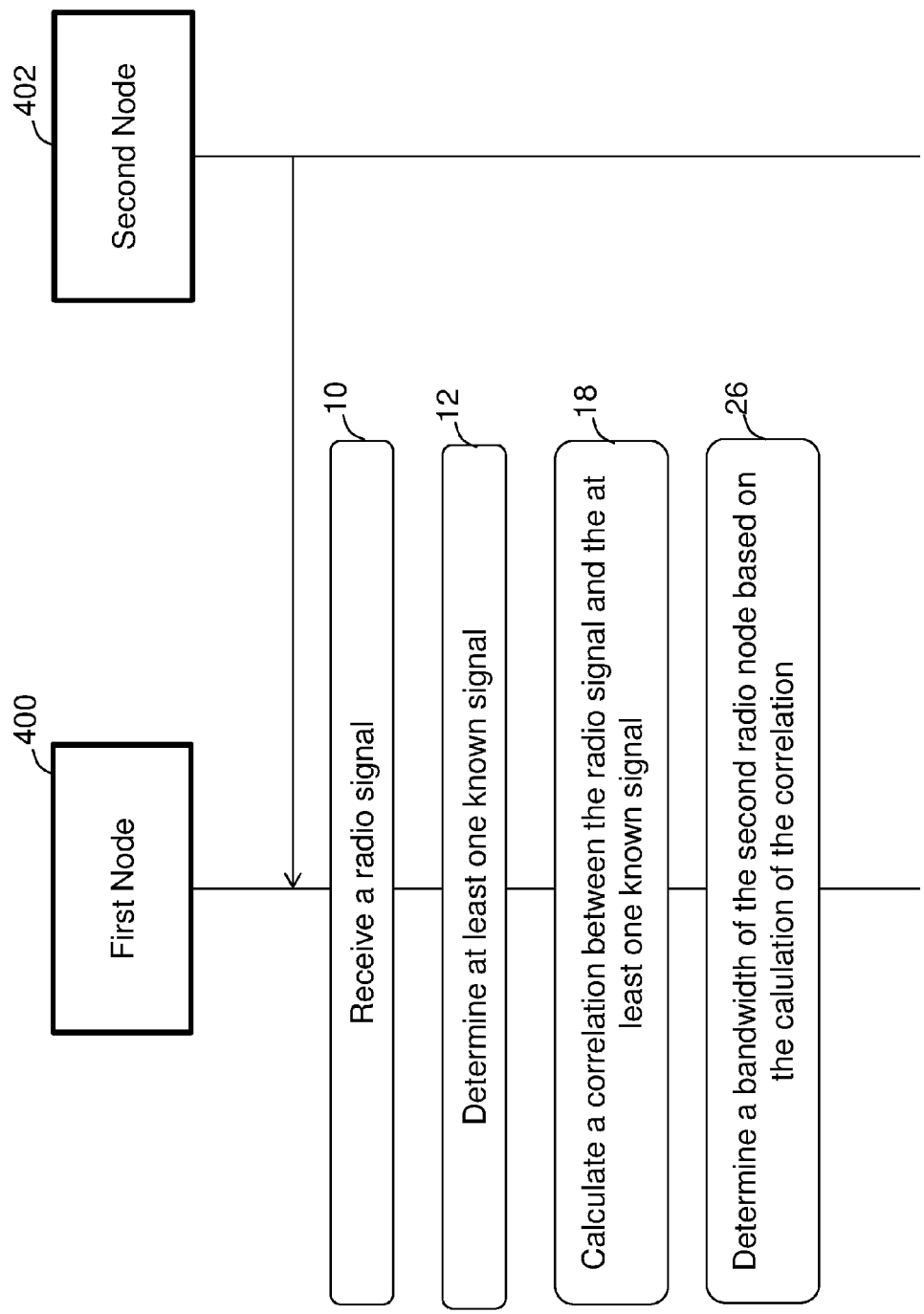
FIG. 5 is a messaging diagram of a first and second radio node for bandwidth determination, according to some of the example embodiments presented herein.

FIG. 5 illustrates an overview of some of the example embodiments presented herein. The example embodiments presented herein are directed towards a first radio node 400, and corresponding method therein, for determining a bandwidth of a second radio node 402. According to some of the example embodiments, the first radio node 400 receives a radio signal from the second radio node 402 (operation 10). Thereafter, the first radio node 400 determines at least one known signal which is transmittable on known resource elements (operation 12). Once the known signal has been determined, a correlation between the received radio signal and the known signal is calculated (operation 18). Based on this correlation, the bandwidth of the second radio node is determined (operation 26).

Accordingly, some of the example embodiments presented herein may be summarized as follows. First, some of the example embodiments presented herein may be directed towards methods in a wireless device of obtaining bandwidth information of a first radio signal transmitted by a radio node (e.g., a wireless device or radio network node). Such a method comprises performing a correlation between a pre-defined first radio signal and radio signal received from the resource elements comprising the first radio signals over pre-defined set of bandwidths. The method may further comprise determining the bandwidths out of the pre-defined set of bandwidths, whose correlation result is above a threshold. The method may also comprise determining the bandwidth of the first radio signal to be the largest bandwidth over which the correlation result is above a threshold.

Some of the example embodiments may be directed towards methods in a wireless device for obtaining bandwidth information of a first radio signal transmitted by a radio node by discovering that the bandwidth of the first signal is not the same as a reference bandwidth, for example, not the same as the serving cell bandwidth. The method further comprises determining the transmission bandwidth of the first radio signal by performing a correlation in frequency domain, for example, between a pre-defined radio signal and radio signal received from the resource elements comprising the first radio signals over pre-defined set of bandwidths.

Some of the example embodiments presented herein are directed towards methods in a wireless device for using the obtained bandwidth information. According to some of the example embodiments, the obtained bandwidth information is used for adapting a receiver and/or the performance a measurement. The obtained bandwidth information may also be used for providing the obtained bandwidth information to another node, for example, a radio network node, a wireless device, and/or a network node.

Some of the example embodiments are directed towards methods in a radio network node of obtaining and using bandwidth information of a radio node, for example, a wireless device or radio network node, by performing a correlation with a radio signal.

Some of the example embodiments are directed towards methods in a wireless device of signaling information to the network node via, for example, obtaining a request or a trigger for sending capability information to the network. The example embodiments may further comprise signaling the capability information to the network node, said capability indicates that the wireless device is capable of determining the bandwidth of a radio signal by performing correlation with a known signal in frequency domain. Some of the example embodiments are directed towards methods in a network node for collecting the bandwidth information from wireless devices, where the bandwidth is determined with at least the use of a correlation.

The remainder of the text is arranged as follows. First, various methods of obtaining bandwidth information in a wireless device is provided under the subheading 'Obtaining bandwidth information in a wireless device'. Such methods are further detailed under subheadings 'Bandwidth determination by correlation', 'Correlation over all possible bandwidths', 'Correlation over a selected set of bandwidths', 'Correlation over differential bandwidths', and 'Determination of a second bandwidth'.

Thereafter, various uses for the bandwidth information are provided under the subheading 'Example uses of the determined bandwidth information'. Examples of how capability information may be exchanged between various nodes for bandwidth determination are provided under the subheading 'Capability'. Under the subheading 'Meeting pre-defined requirements and tests', various requirements which may be placed on bandwidth determination, according to the example embodiments presented herein, are discussed. Example embodiments related to bandwidth determination in a radio network node and a network node are also provided under the subheadings 'Obtaining and using bandwidth information in a radio network node' and 'Obtaining and using bandwidth information in a network node', respectively.

Finally, an example node configuration and example node operations for the first radio node of FIG. 5 are provided under the subheadings 'Example node configurations' and 'Example node operations', respectively.

Obtaining Bandwidth Information in a Wireless Device

According to some of the example embodiments, a wireless device capable of receiving signals from a radio node, obtains the bandwidth of a radio signal, transmitted by the radio node, by performing a correlation between a known radio signal and the radio signal transmitted by the radio node.

The bandwidth may be obtained by determining a transmission bandwidth of the radio signal. The bandwidth may also be obtained by determining a transmission bandwidth of the radio node or cell. The sub-section entitled 'Bandwidth information' provides definitions of the transmission bandwidth of a radio node or cell. The bandwidth may also be obtained by selecting a transmission bandwidth of the radio signal from a set of pre-defined transmission bandwidths, for example, based on a rule that the selected bandwidth is characterized by the highest correlation result.

The bandwidth may also be obtained via a determination of how the transmission bandwidth relates to a reference bandwidth. For example, the relating may comprise a comparison of a certain value of the transmission and reference bandwidths with respect to a same or different value, for example, X MHz or Y RBs. The relating may also comprise a comparison of a bandwidth of a cell associated with the transmission and reference bandwidth. The relating may further comprise a comparison of the reference value with that of a threshold, for example, the difference between the transmission and reference bandwidth should not be more than Z MHz than a reference value, etc.

According to some of the example embodiments, the determining may also take into account additional information, for example, obtained by the wireless device autonomously, acquired from memory or stored data, or received from another node. Such information may comprise center frequency information. The obtained information may also comprise timing information about the radio signal, for example, time synchronization, SFN information, radio frame alignment, etc. The obtained information may comprise an indication on whether the transmission bandwidth configuration comprises an odd or an even number of RBs. Furthermore, the obtained information may comprise characteristics of the radio signal.

According to some of the example embodiments, the determining bandwidth may further comprise determining the unknown center frequency of the transmission bandwidth. According to some of the example embodiments, the determining may further comprise determining of a second bandwidth.

Bandwidth Determination by Correlation

According to some of the example embodiments, determining the bandwidth by correlation comprises correlation of a received signal to a known signal sequence. The known signal sequence is transmitted in known, or hypothetically known, resource elements (REs) which typically are a subset of all REs. For instance, assuming CRSs (Antenna port 0 or 1), these are transmitted every 6th sub-carrier in OFDM symbol 0, 4, 7, 11 (long CP) in every subframe. The phase shift of CRS is dependent on the PCI and is defined in the 3GPP specifications. Since the device has detected the cell with an unknown BW (during the cell search step), and hence PCI is known, the device knows the timing and hence also the positions (REs) where possible CRSs may be found. What is not known is the BW of the cell but for each BW the potential REs for CRSs are known.

Hence this information is used in the correlation step for the determination of the BW. It should be appreciated that the use of CRSs is just an example and other known signals may also be covered by the some of the example embodiments. Examples of other signals known to the user equipment, for example, pre-coded in the user equipment, and that are transmitted over a variable bandwidth in a cell are PRS, CSI-RS, DM-RS, RS, etc.

According to some of the example embodiments, the known signal sequence may be determined by known characteristics of the radio signal. Such known characteristics may comprise any one or more of a signal type, radio node identification (e.g., PCI), pseudo-random number generator parameters (if it is used for generating the sequence), associated time and/or frequency resources (e.g., subframe number, slot number, subcarrier number, resource block, etc.), and even or odd number of RBs comprised in the bandwidth.

The above information may be determined based on a pre-defined rule. An example of a pre-defined rule is knowing that CRS is always transmitted in a cell at certain resource elements (REs) and the transmission bandwidth is the cell transmission bandwidth configuration and/or received from another node. The transmission may be done for determining the bandwidth or even for some other purposes, for example, assistance data for device-to-device communication, assistance data for positioning, assistance data for inter-cell interference coordination or aggressor interferers' information for user equipment in a cell range extension zone in a heterogeneous network.

According to some of the example embodiments, multiple hypotheses may be tested to determine the bandwidth. According to some of the example embodiments, the bandwidth determination may be performed in steps when one or more bandwidth candidates are confirmed or rejected at each step. For such an iterative approach, for example, a golden section search approach may be adapted.

As an example, an iterative approach may comprise assuming that 1.4 MHz is always the minimum and the radio node is active, thereafter a test is performed in sequence whether the transmission bandwidth is 5 MHz, 10 MHz, 15 MHz, or 20 MHz. As another example, an iterative approach may comprise assuming that it is not known whether the radio node is active, and thereafter a test at 1.4 MHz, and then at 10 MHz (if 1.4 MHz is confirmed by correlation) and 5 MHz (otherwise), 20 MHz (if 10 MHz is confirmed) and 15 MHz (otherwise).

According to some of the example embodiments, the correlation may be performed over parts of the bandwidth being tested/verified, for example, to account for frequency-selective fading and/or exploiting the iterative approach. According to some of the example embodiments, the final correlation result may be a combination of the correlation results associated with the parts of the bandwidth.

Figure 6:
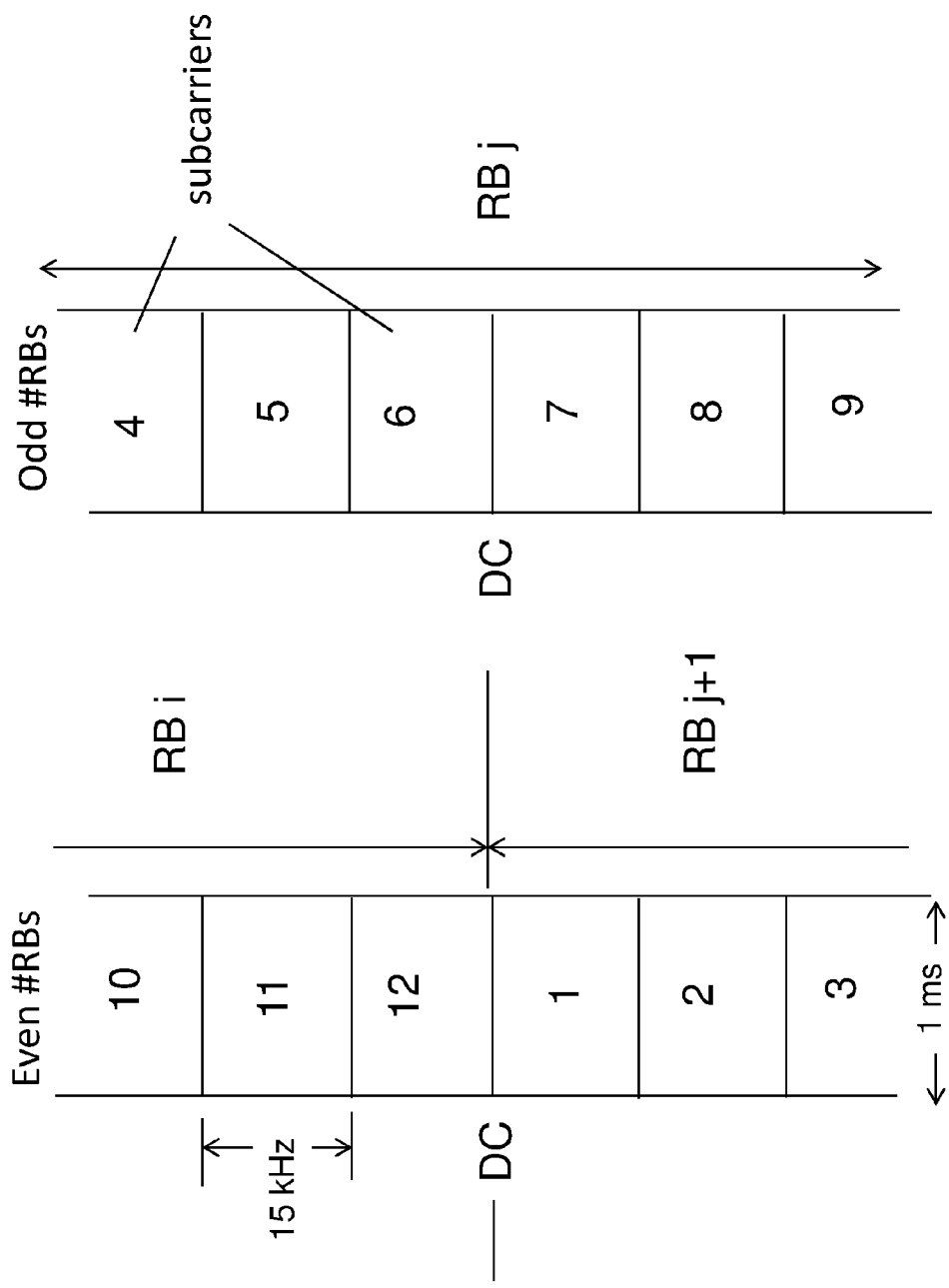
FIG. 6 is another illustrate example of a bandwidth configuration, according to some of the example embodiments presented herein.

In LTE, the transmission bandwidth configuration may comprise an even or odd number of RBs, for example, 6 RBs for 1.4 MHz and 25 RBs for 5 MHz. Depending on the bandwidth, the center frequency, for example, the DC carrier which is not transmitted is used in DL, may be either between the two center RBs or in the middle of a center RB, as illustrated in FIG. 6.

Some physical signals, for example, PSS, SSS, or CRS are transmitted symmetrically with respect to the center frequency which divides their transmission BW by half. However, in some cases the transmission bandwidth may be not symmetric with respect to the channel bandwidth center, for example, demodulation signals may follow a scheduling pattern. Furthermore, some of the signals, for example, CRS and PBCH, currently carrying the bandwidth information, may not be transmitted in a new carrier type for interference reduction and energy efficiency purpose.

Therefore, according to some of the example embodiments, the correlation may also take into account whether the transmission bandwidth configuration comprises even or odd number of RBs, which determines the RE mapping for the correlated signal, and their configuration with respect to the center. In one example, the signal sampling and/or correlation may be performed differently for the same type of signal for even number of RBs and odd number of RBs and depending on whether DC is comprised within a RB or not.

Correlation Over all Possible Bandwidths

According to some of the example embodiments, the wireless device first obtains correlation for the first radio signals over all possible or pre-defined set of bandwidths, for example, 1.4 MHz, 3 MHz, 5 MHz, 10 MHz, 15 MHz and 20 MHz in LTE. In the next step, the wireless device checks for the maximum correlation and determines the BW which corresponds to the maximum correlation.

According to some of the example embodiments, the wireless device performs or calculates a correlation between pre-defined first radio signals and radio signals which are received from the resource element (RE) carrying the first radio signals over k set of pre-defined bandwidths ($B_1$, $B_2$, . . . , $B_K$) of the first radio signals. The output of the correlations on the log scale for a set of K bandwidths are ($\Gamma_{RS\_1}$, $\Gamma_{RS\_2}$, . . . , $\Gamma_{RS\_K}$).

Thereafter, the determined bandwidth (B) of the first radio signals may correspond to the maximum correlation value using any number of evaluations. An example of such an evaluation is $B=B_M$, where M is the index of the maximum BW derived from all valid correlation values. The correlation value, $\Gamma_{RS\_i}$, is considered valid if it is above a threshold, for example, $\Gamma_{RS\_i} \geq \Psi$, where $\Psi$ may be set to 0 dB and $1 \leq i \leq K$.

Another example of such an evaluation may provide that more than one candidate may also be determined, for example, the candidates with a correlation result above a threshold. Thereafter, one of these candidates may further be selected, for example, based on another correlation, based on the estimated probability for each bandwidth candidate taking into account other factors or other measurements, or by any other approach.

Correlation Over a Selected Set of Bandwidths

According to some of the example embodiments, the wireless device may calculate the correlation for the first radio signals for the pre-defined set of bandwidths in steps and compare the correlation output with that of the previous output in each step. The wireless device stops calculating the correlation for the next remaining pre-defined bandwidths provided the correlation is below a threshold or until all BWs are checked. The determined BW is the maximum BW of the correlation value which is above a threshold, for example, a valid correlation. The step wide correlation may be performed in ascending or descending order of the size of the bandwidths.

In general, assume there are K pre-defined BWs, more specifically, K=6. Therefore, the pre-defined bandwidths may be 1.4, 3, 5, 10, 15 and 20 MHz, which are denoted by B1, B2, B3, B4, B5 and B6 respectively.

According to some of the example embodiments, the K pre-defined BWs are correlated in ascending order of BW. Thus, initially, i=0; where 1≤i≤K. Upon the completion of each iteration, i=i+1. During an iteration, a correlation between pre-defined first radio signals and the radio signals received from the resource element (RE) is calculated. The first radio signal is carried over a pre-defined bandwidth ($B_i$) of the first radio signals, wherein the output of the correlations on the log scale is ($\Gamma_{RS\_i}$).

During each iteration, it is determined whether the correlation is valid. This determination is provided by considering if the correlation value, $\Gamma_{RS\_i}$, is above a threshold, for example, $\Gamma_{RS\_i} \geq \Psi$, where $\Psi$ may be set to 0 dB. If $\Gamma_{RS\_i}$ is found to be valid and i<K, another iteration or correlation may be calculated. If $\Gamma_{RS\_i}$ is found to be invalid, the bandwidth (B) of the first radio signals is determined to be the bandwidth corresponding to the maximum bandwidth of all the valid correlation values.

According to some of the example embodiments, the K pre-defined BWs are correlated in descending order. Thus, initially, i=K+1, where 1≤i≤K. Upon the completion of each iteration, i=i-1. During an iteration, a correlation between pre-defined first radio signals and the radio signals received from the resource element (RE) is calculated. The first radio signal is carried over a pre-defined bandwidth ($B_i$) of the first radio signals, wherein the output of the correlations on the log scale is ($\Gamma_{RS\_i}$).

During each iteration, it is determined whether the correlation is valid. This determination is provided by considering if the correlation value, $\Gamma_{RS\_i}$, is above a threshold, for example, $\Gamma_{RS\_i} \geq \Psi$, where $\Psi$ may be set to 0 dB. If $\Gamma_{RS\_i}$ is found to be valid and i>1, another iteration or correlation may be calculated. If $\Gamma_{RS\_i}$ is found to be invalid, the bandwidth (B) of the first radio signals is determined to be the bandwidth corresponding to the maximum bandwidth of all the valid correlation values.

Correlation Over Differential Bandwidth

According to some of the example embodiments, correlation is performed over a bandwidth in a differential manner. In the following example, bandwidths 1.4, 3, 5, 10, 15 and 20 MHz are denoted by $B_{min}$, B1, B2, B3, B4 and B5 respectively.

According to such example embodiments, the wireless device initially performs the correlation between pre-defined first radio signals and the radio signals received from the resource element (RE) carrying the first radio signal over the smallest possible BW ($B_{min}$), for example, 1.4 MHz. This is done to ensure that the wireless device is well synchronized to the cell whose BW is being determined.

In subsequent steps, the wireless device calculates a correlation for the first radio signals over a differential set of RBs. This latter step is repeated until the output of the correlation is not valid or all differential set of RBs are checked by correlation. The determined BW is the largest BW corresponding to the valid correlation over all differential set of RBs. According to this example embodiment, the correlation value, $\Gamma_{RS\_i}$, is considered valid if it is above a threshold, for example, $\Gamma_{RS\_i} \geq \Psi$, where $\Psi$ can be set to 0 dB.

According to some of the example embodiments, the differential set of RBs ($RB_{diff}$) may be expressed in different manners. For example, $RB_{diff}$ is the uncommon or non-overlapping resource blocks between $BW_{min}$ and $BW > BW_{min}$. $RB_{diff}$ is the uncommon or non-overlapping resource blocks between any two successive bandwidths, for example, between B2 and B3. This has an example advantage of performing correlation over fewer RBs in subsequent steps.

To elaborate on the first example, let $\Gamma_{RS\_1}$, $\Gamma_{RS\_2}$, $\Gamma_{RS\_3}$, $\Gamma_{RS\_4}$, and $\Gamma_{RS\_5}$ be the results of the correlation calculated by the wireless device for first radio signals in the resource elements within the differential RBs over (B1−Bmin), (B2−Bmin), (B3−Bmin), (B4−Bmin) and (B5−Bmin), respectively. Assume that the wireless device starts with a set (B1−Bmin) and determines that the correlation until another set (B3−Bmin) is valid. Therefore, the determined BW of that first signal is assumed to be 5 MHz.

In a second example of correlation over differential RBs, let $\Gamma_{RS\_min-1}$, $\Gamma_{RS\_1-2}$, $\Gamma_{RS\_2-3}$ and $\Gamma_{RS\_3-4}$, and $\Gamma_{RS\_4-5}$ be the results of the correlation performed by the wireless device for first radio signals in the resource elements within the differential RBs over (B1−Bmin), (B2−B1), (B3−B2), (B4−B3) and (B5−B4), respectively. For example, if the wireless device starts with set (B1−Bmin) and determines that the correlation until set (B4−B3) is valid, the determined BW of that first signal is assumed to be 10 MHz.

Determination of a Second Bandwidth

According to some of the example embodiments, a second bandwidth, and/or its center frequency, is determined based on the determined radio signal transmission bandwidth. The second bandwidth may be associated with the same radio node as the transmission bandwidth or with another radio node.

According to some of the example embodiments, the second bandwidth, or information associated with the second bandwidth may comprise a channel bandwidth. The channel bandwidth may be based on a pre-defined rule relating the determined transmission bandwidth and the channel bandwidth. The second bandwidth, or associated information, may comprise a transmission bandwidth configuration. The second bandwidth, or associated information, may also be a transmission bandwidth, for example, of another signal or channel of the same radio node or a signal or channel transmitted by another radio node.

According to some of the example embodiments, the second bandwidth, or associated information, may comprise a subband bandwidth, an aggregated bandwidth or a measurement bandwidth. The second bandwidth, or associated information, may comprise a transmission signal configuration, for example, selecting one from a set of pre-defined configurations which matches the determined transmission bandwidth. The second bandwidth, or associated information, may comprise the overlap in the frequency domain, for example counted in RBs, MHz, portion or percentage, of the determined transmission bandwidth and a reference bandwidth, for example a serving cell bandwidth.

According to some of the example embodiments, the determining of the second bandwidth, or associated information, may be provided in a number of ways. One example method of determination may comprise the use of a pre-defined rule relating to the determined transmission bandwidth with the second bandwidth. A further example method is the use of a pre-defined rule relating the radio signal for which the transmission bandwidth has been determined and a radio signal for which the second bandwidth is determined.

Yet a further example method of determination is the use of multiple determined transmission bandwidths, for example, when the second bandwidth is the aggregated bandwidth. Another example method of determination is via the performance of an additional measurement or correlation, etc.

Example Uses of the Determined Bandwidth Information

The determined bandwidth information, which may comprise a first and/or second bandwidth, may comprise different forms of information. Examples of such information may comprise the determined transmission bandwidth or its relation to a reference bandwidth, the determined center frequency, the determined second bandwidth, and/or a function of one or more determined bandwidths such as minimum, maximum, median, a certain percentile of bandwidths of all detected cells.

The determined bandwidth information for one or more radio signals on one or more carrier frequencies may be further used by the wireless device. An example of such a use is adapting a receiver of the radio node for performing, for example, a measurement, for example, a RRM or RLM measurement, channel state estimation, receiving and demodulation a channel, etc.

According to some of the example embodiments, the adaption of the receiver may comprise selecting a receiver type, for example, using an IC receiver when the aggressor signal bandwidth may be determined by the wireless device. The receiver adaption may further comprise configuring a measurement bandwidth for radio signals for which the determined bandwidth applies. The receiver adaptation may also comprise selecting aggressor interferers and estimating the channel for the selected aggressor interferers to mitigate, for example, cancel the determined aggressor interference over the determined bandwidth overlapping with the victim radio signal. The receiver adaption may also comprise adapting a measurement procedure.

Figure 1B:
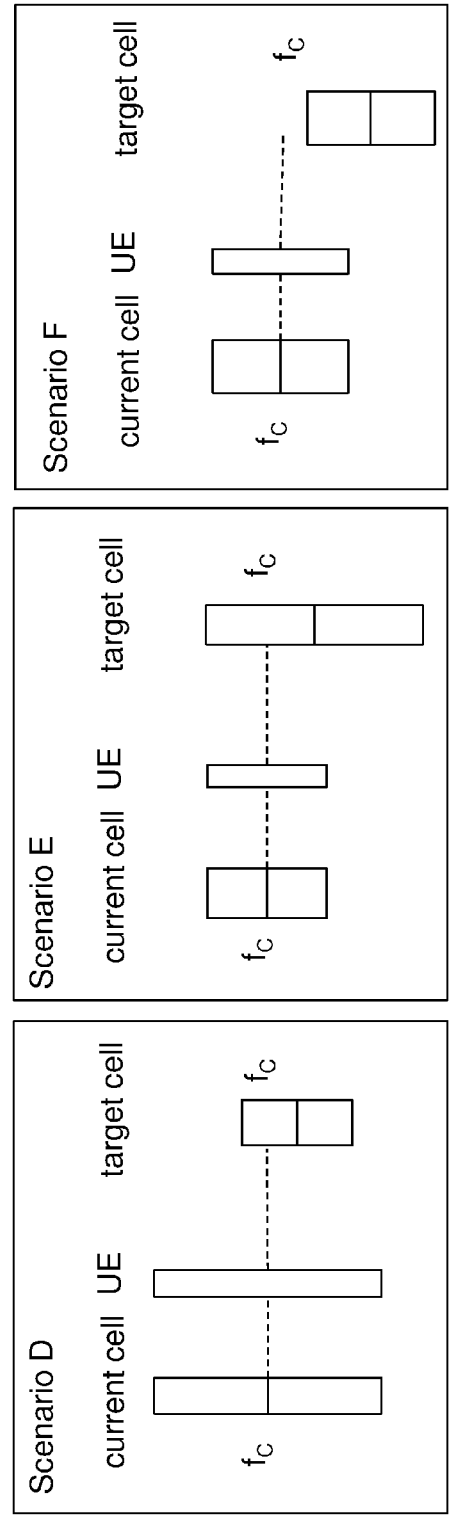
Figure 2A:
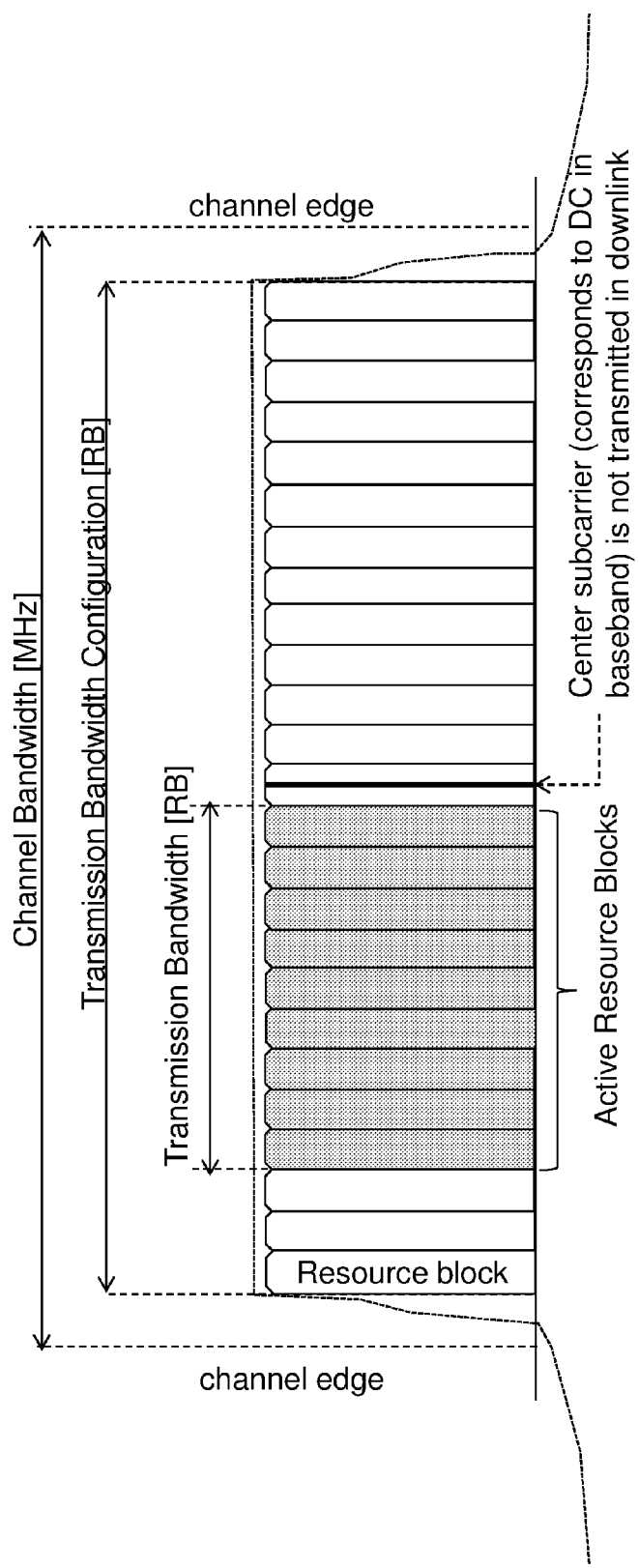
FIG. 2A is a channel bandwidth and transmission bandwidth configuration for a E-UTRA carrier.
Figure 2B:
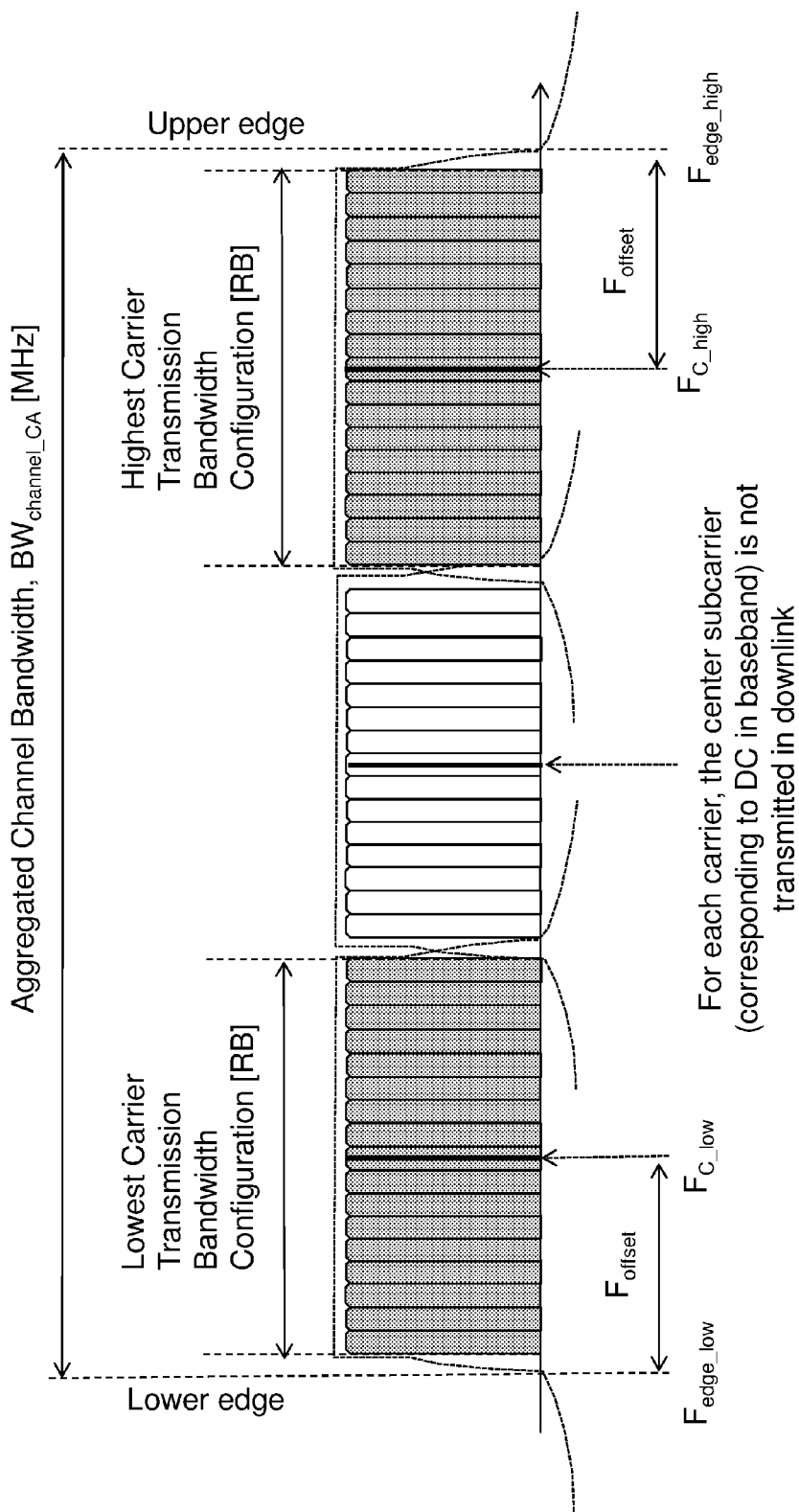
FIG. 2B is an aggregated channel bandwidth for an intra-band carrier aggregation.
Figure 2C:
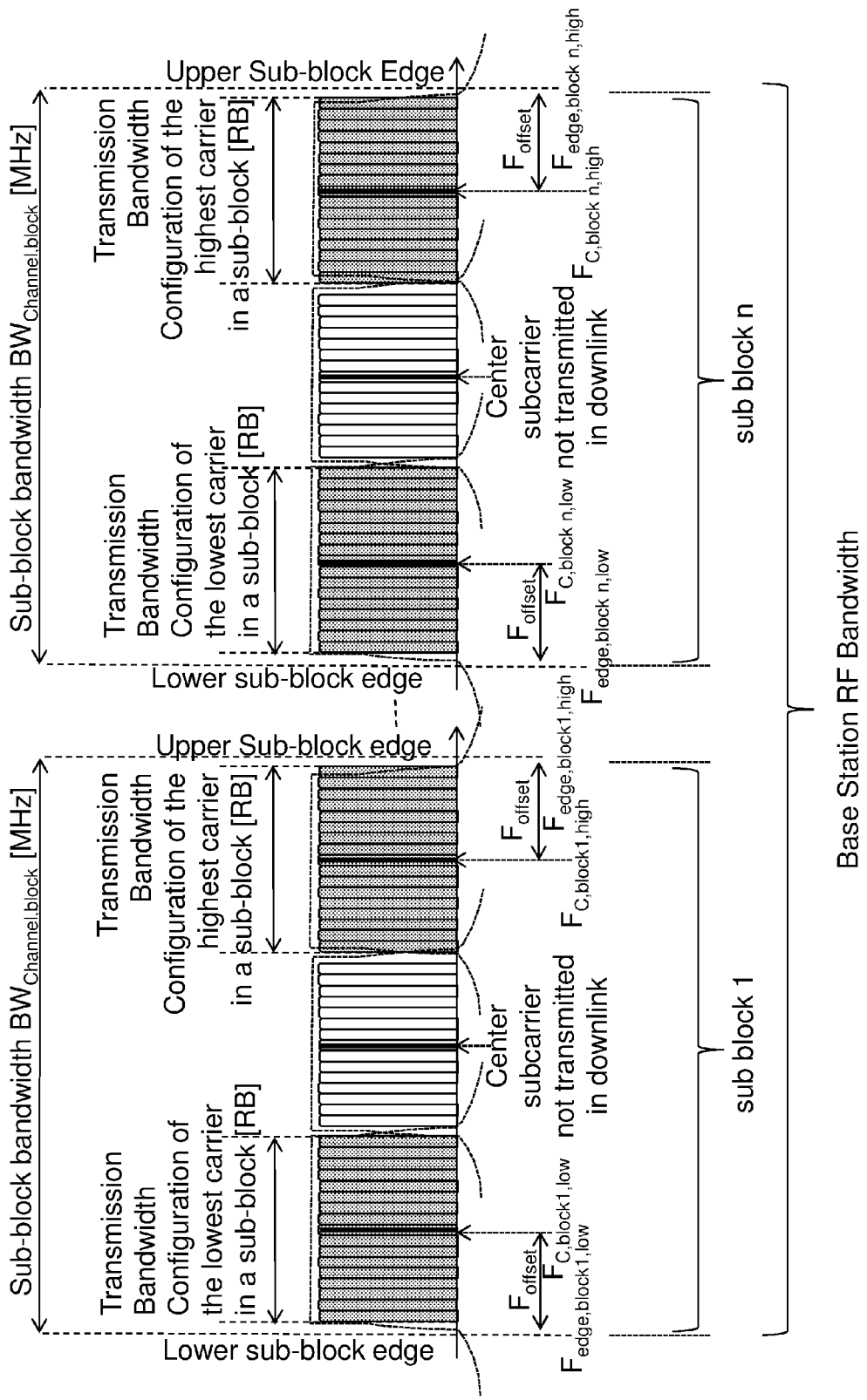
FIG. 2C is a sub-block bandwidth for an intra-band non-contiguous spectrum.

According to some of the example embodiments, another example use is categorizing or grouping the radio node's transmissions. An example of such a category or group is intra-frequency or inter-frequency, which is illustrated in FIGS. 1a and 1b. Transmissions which are grouped in this category may have measurements performed accordingly and/or reporting the categorized nodes to another node may be performed. Furthermore, grouping by bandwidth, for example, radio nodes with the same or similar bandwidth are may also be provided in a same group.

According to some of the example embodiments, another example use of the bandwidth information is verifying the bandwidth information available from other sources or obtained earlier. A further example use of the bandwidth information is determining activity of the radio node. Yet another example use of the bandwidth information is performing interference coordination, for example, avoid transmitting at least some signals on resources over the determined bandwidth to avoid or minimize interference Yet another example use of the bandwidth information is signaling of the determined bandwidth information to another wireless device. Another example use of the bandwidth information is signaling the determined bandwidth information to a network node, for example, to an eNodeB or positioning node.

Capability

It should be appreciated that not all wireless devices may be mandated to implement the determining of the bandwidth of radio signals based on correlation in the frequency domain, according to the example embodiments presented herein. Therefore, the capability of the wireless device to perform bandwidth determination might be signaled to another node, for example, to be used for measurement configuration, HO decision, assistance data build up, etc.

According to some of the example embodiments, a wireless device may also signal more detailed information related to its supported capability of determining bandwidth of radio signals by performing correlation in frequency domain. An example of such additional information is the capability of determining bandwidth of certain type of radio signals, for example, CRS, PRS, etc. A further example of additional information is the capability of determining the bandwidth of a cell for any type of radio signals.

Yet a further example of such additional information is the capability of determining the bandwidth of radio signals only for cells on a serving carrier frequency. A further example of additional information is the capability of determining the bandwidth of radio signals for cells on a primary serving carrier frequency as well as on one or more non-serving carrier frequencies, for example, an inter-frequency carrier, and/or on one or more SCCs.

Another example of additional information is the capability of determining the bandwidth of radio signals for cells on a primary serving carrier frequency and on one or more SCCs for a certain type of carrier aggregation, for example, when a wireless device has multiple receivers, inter-band CA, intra-band non-contiguous CA, etc. A further example of additional information is the capability of determining the bandwidth of radio signals for cells in another RAT or another RAN.

According to some of the example embodiments, a wireless device may have such capability if it is capable of operating in certain scenarios. For example, wireless devices not capable of PBCH IC may have to implement at least the basic embodiment of Section 4, especially in networks with radio frame alignment (e.g., synchronous networks and/or TDD networks and/or network implementing eICIC/FeICIC).

In another example, wireless devices capable of operating on a new carrier type may need to implement the example embodiments presented under the subheading 'Obtaining bandwidth information in a wireless device'. In yet another example, wireless devices capable of mitigating the interference from home eNBs may implement the example embodiments presented under the subheading 'Obtaining bandwidth information in a wireless device'. In yet a further example, wireless devices supporting enhanced receivers, for example, supporting interference cancellation, may implement the example embodiments presented under the subheading 'Obtaining bandwidth information in a wireless device'.

According to some of the example embodiments, the wireless device may send the capability information to the network node. According to some of the example embodiments, the capability information may be sent via proactive reporting without receiving any explicit request from the network node, for example, serving or any target network node.

According to some of the example embodiments, the capability information is sent via a reporting upon receiving any explicit request from the network node, for example, a serving or any target network node. According to some of the example embodiments, the capability information is sent via an explicit request sent to the wireless device by the network at any time or at any specific occasion. For example, the explicit request for the capability reporting may be sent to the wireless device during an initial setup or after a cell change, for example, handover, RRC connection re-establishment, RRC connection release with redirection, PCell change in CA, PCC change in PCC, etc.

The network uses the received wireless device capability information for one or more operations. For example, if the wireless device supports this capability then the network may not signal the BW of one or more cells to the wireless device since it may determine such information itself. The network may also forward capability information to the neighboring or target network node at the time of a cell change. Thus, the target network node does not have to acquire the capability again from the wireless device.

Meeting Pre-Defined Requirements and Tests

According to some of the example embodiments, a wireless device, or a radio node, in general, determining one or more transmission bandwidths by correlation may meet one or more pre-defined requirements. Some example requirements are measurement time, reporting time, error probability, etc. The requirements may additional depend on one or more conditions, for example, signal strength, signal quality, interference characteristics, number of strong interferers, activity state, for example, DRX, non-DRX, etc.

The requirement may be different for determining a transmission bandwidth for the radio nodes with the capability described above and radio nodes without such capability. For example, a radio node determining the transmission bandwidth by correlation should be able to determine the bandwidth within time T1, whilst a radio node determining the transmission bandwidth by other means, such as PBCH reading, should be able to determine the bandwidth within time T2, where T2 may be different from T1.

According to some of the example embodiments, in a test, a radio node prior to using the determined bandwidth, for example, for handling interference from an aggressor cell, may also be required to first determine the bandwidth within a certain time, depending on the conditions or radio node capability described above, etc.

Obtaining and Using Bandwidth Information in a Radio Network Node

The example embodiments presented under this subheading are similar to those presented under the subheading entitled 'Obtaining bandwidth information in a wireless device', but under the current subheading, such methods are instead implemented in a radio network node. Therefore, all embodiments described under the subheading 'Obtaining bandwidth information in a wireless device', may also be applied to a radio network node. It should be appreciated that the signaling of the determined bandwidth information to another radio network node may be provided via an X2 interface.

According to some of the example embodiments, a radio network node obtains the bandwidth of a radio node, for example, a wireless device or a radio network node, by calculating a correlation with a radio signal transmitted by the radio node.

According to some of the example embodiments, the bandwidth may be obtained by determining transmission bandwidth of the radio signal. The bandwidth may also be obtained by selecting a transmission bandwidth of the radio signal from a set of pre-defined transmission bandwidths, for example, based on a rule that the selected bandwidth is characterized by the highest correlation result.

The bandwidth may further be obtained by determining how the transmission bandwidth relates to a reference bandwidth. The relating may comprise determining if a certain value is the same or different, for example, X MHz or Y RBs. The relating may further comprise determining if a cell's bandwidth is the same of different. The relating may also comprise determining if a reference value is not more different than Z MHz.

Obtaining and Using Bandwidth Information in a Network Node

According to some of the example embodiments, a network node obtains the bandwidth information from a wireless device upon a request or in an unsolicited way, periodically or on an event-triggered basis. Some examples of the network node are a radio network node, for example, an eNodeB, relay, femto BS, LMU, etc. Further examples of a network node is a network node without radio interface, for example, positioning node, O&M, SON node, MDT node, a coordinating node, a gateway node, etc.

The bandwidth information may comprise, for example, a determined transmission bandwidth or its relation to a reference bandwidth, a determined center frequency, a determined second bandwidth, and/or a function of multiple bandwidths. The function of multiple bandwidths may comprise, for example, the minimum or maximum of all bandwidths of the detected cells, where the cells' PCIs may also be reported.

According to some of the example embodiments, the bandwidth information may be the bandwidth information obtained with the example embodiments presented under the subheading entitled 'Obtaining bandwidth information in a wireless device'. It should be appreciated that the bandwidth information may be obtained in other one or more ways which may or may not comprise the example embodiments presented under the subheading entitled 'Obtaining bandwidth information in a wireless device'.

The bandwidth information obtained from one or more wireless devices may be used by the network node. Example uses for the obtained bandwidth information are network planning and optimization, MDT, positioning, RRM, inter-cell interference coordination, and/or neighbor cell relation build up and update. A further example use is for building up assistance data, which may be, for example, positioning assistance data, aggressor interferer information as for eICIC/FeICIC, etc.

A further example use is measurement configuration for the wireless device. Another example use for the obtained bandwidth information is deciding an aggregate indicator indicating the bandwidth of multiple radio nodes and signaling the indicator. The signaling of the indication may be via RRC in broadcast or dedicated signaling or via a control channel to another node, for example, to a wireless device or to another network node, which is currently not possible in 3GPP specifications. An example indicator may be "all cells are using the same bandwidth" (yes/no) or "at least N cells or radio nodes are using bandwidth larger than threshold", for example, N=1 or 4, threshold=5 MHz or "at least N cells or radio nodes are using bandwidth smaller than threshold".

A further example use of the obtained bandwidth information is configuring the allowedMeasBandwidth parameter sent via RRC to wireless devices, as provided in 3GPP specification TS 36.331. Such configuration may be used for mobility purposes and/or for configuring wideband measurements such as wide-band RSRQ.

Example Node Configurations

Figure 7:
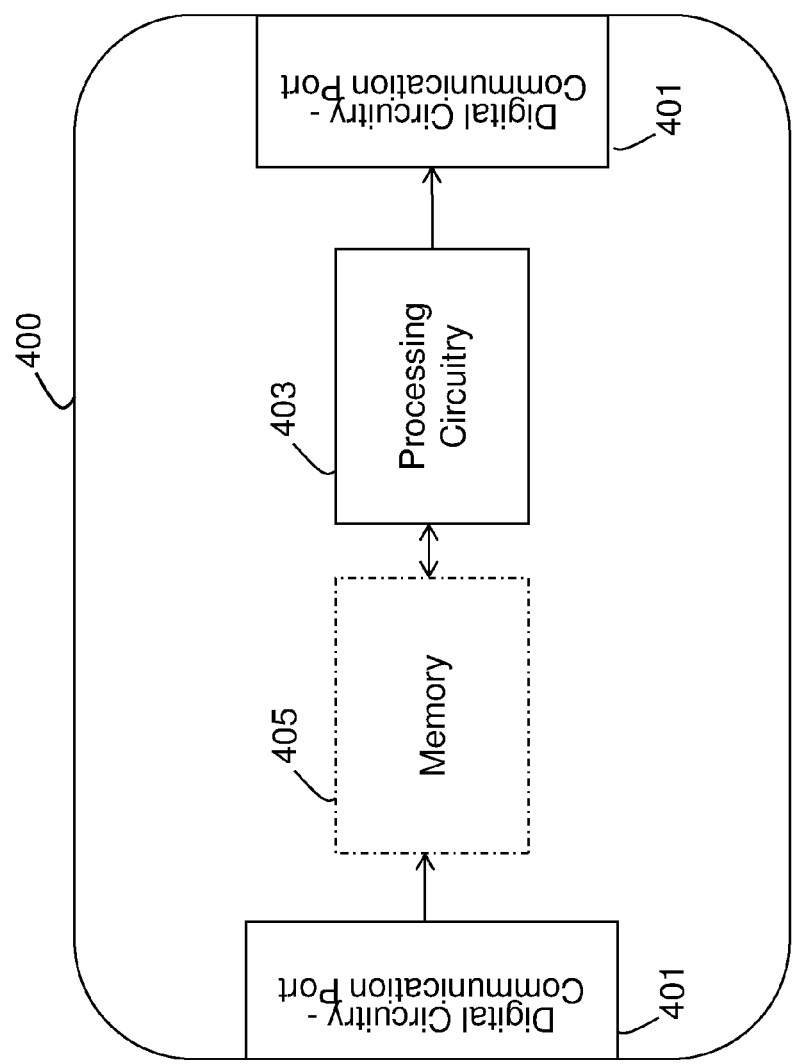
FIG. 7 is an example node configuration of the first radio node of FIG. 5, according to some of the example embodiments presented herein.

FIG. 7 provides an example of node a configuration of the first node 400 of FIG. 5. According to some of the example embodiments, the first radio node is a wireless device, a radio node, a radio network node, a base station, a remove radio unit, a remove radio head, an access point, a location measurement unit or any other node in the network that may be configured to perform the example embodiments presented herein.

The example configuration of FIG. 7 may comprise digital circuitry or a communication port 401 that may be configured to receive and/or transmit communication data, instructions, and/or messages. It should be appreciated that the digital circuitry or communication port 401 may be comprised as any number of transmitting and/or receiving units or circuitry. It should further be appreciated that the digital circuitry or communication port 401 may be in the form of any input or output communications port known in the art. The digital circuitry or communication port 401 may comprise RF circuitry and baseband processing circuitry.

The example node configuration may also comprise a processing unit or circuitry 403 which may be configured to perform any of the example embodiments presented herein. The processing circuitry 403 may be any suitable type of computation unit, e.g. a microprocessor, digital signal processor (DSP), field programmable gate array (FPGA), or application specific integrated circuit (ASIC), or any other form of circuitry. The example node configuration may further comprise a memory unit or circuitry 405 which may be any suitable type of computer readable memory and may be of volatile and/or non-volatile type. The memory may be configured to store received, transmitted, and/or measured data, device parameters, communication priorities, and/or executable program instructions.

Figure 8:
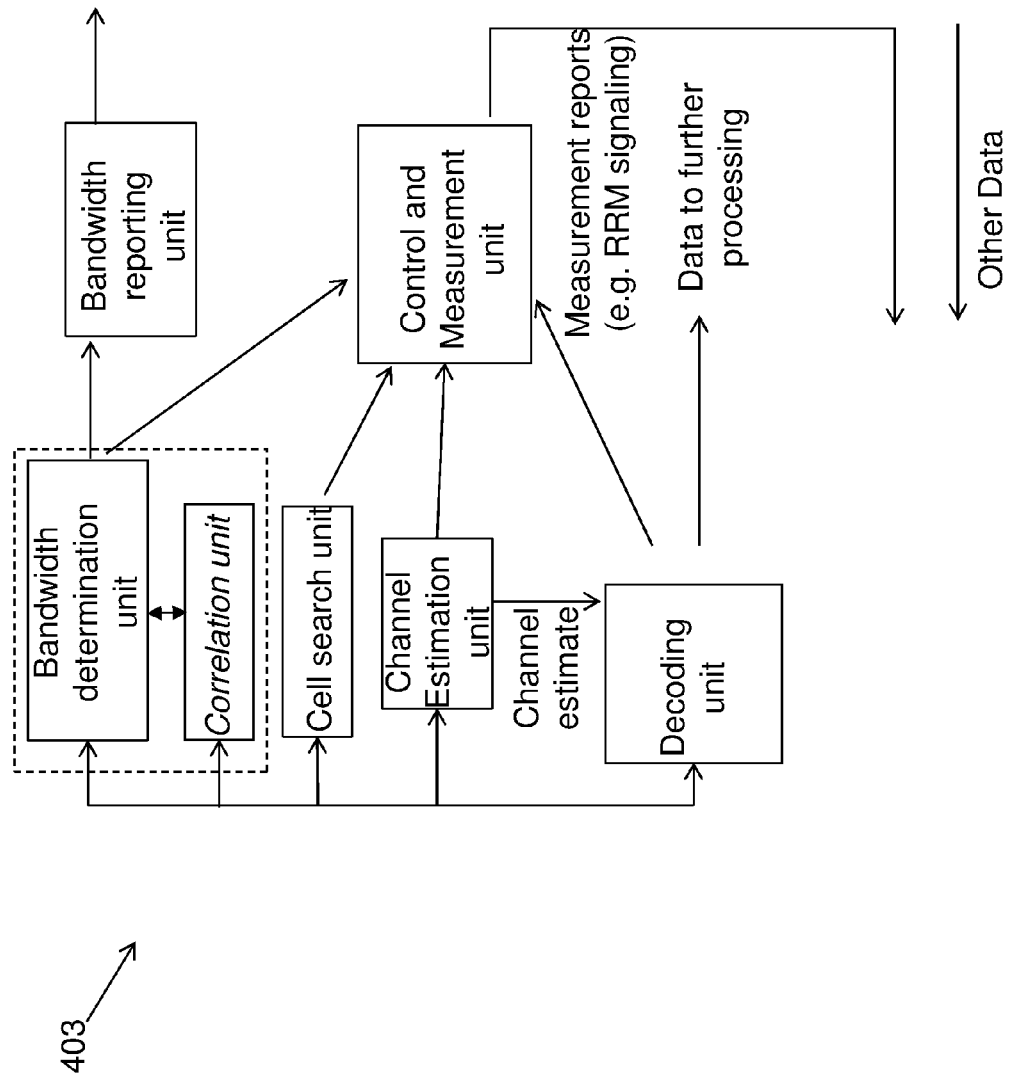
FIG. 8 is an example of the processing circuitry of the first radio node of FIGS. 5 and 7, according to some of the example embodiments presented herein.

FIG. 8 is a detailed example of units which may be comprised in the processing circuitry 403 of FIG. 7. As illustrated in FIG. 8, the processing circuitry 403 may comprise a bandwidth determination unit and a correlation unit which is configured to determine the bandwidth of a second radio node as discussed herein. The bandwidth determination unit and/or the correlation unit may be in communication with a bandwidth reporting unit. The bandwidth reporting unit may report the determined bandwidth to neighboring nodes as discussed herein.

The bandwidth determination unit and/or correlation unit may also be in communication with a control and measurement unit. The control and measurement unit may use the determined bandwidth for measurement configuration, interference management, etc., as discussed herein. It should be appreciated that a cell search unit, channel estimation unit and decoding unit may also make use of the determined bandwidth as discussed herein.

Example Node Operations

Figure 9:
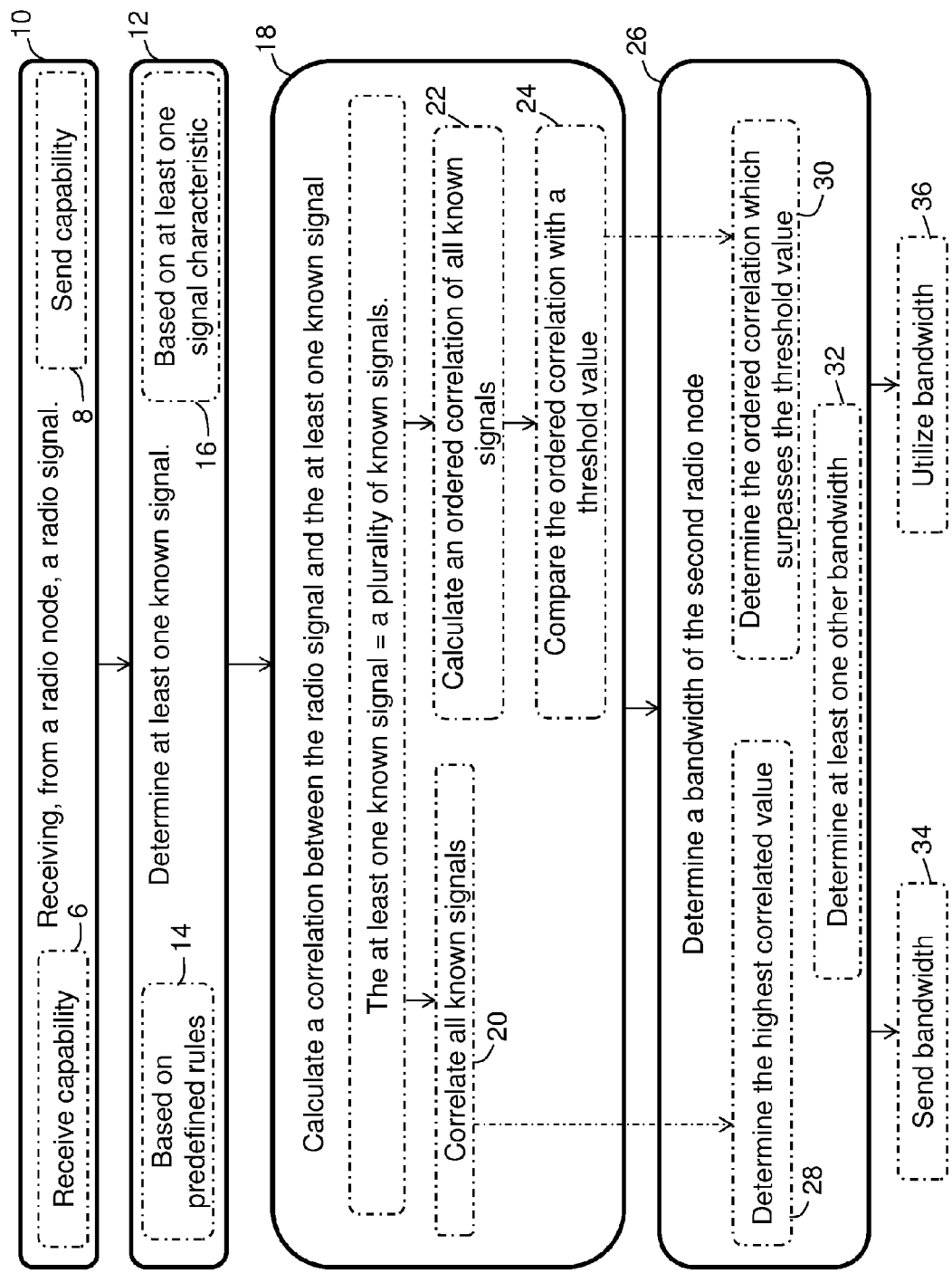
FIG. 9 is a flow diagram depicting example operations of the first radio node of FIGS. 5, 7 and 8, according to some of the example embodiments presented herein.

FIG. 9 a flow diagram depicting example operations which may be taken by a first radio node. According to some of the example embodiments, the first radio node is a wireless device, a radio node, a radio network node, a base station, a remove radio unit, a remove radio head, an access point, a location measurement unit or any other node in the network that may be configured to perform the example embodiments presented herein (e.g., the node of FIG. 7). FIG. 9 is directed towards operations in a first radio node for determining a bandwidth of a second radio node. The first and second radio nodes are configured for use in a communications network.

It should also be appreciated that the flow diagram illustrated below comprises some operations which are illustrated with a solid border and some operations which are illustrated with a dashed border. The operations which are comprised in a solid border are operations which are comprised in the broadest example embodiment. The operations which are comprised in a dashed border are example embodiments which may be comprised in, or a part of, or are further operations which may be taken in addition to the operations of the boarder example embodiments. It should be appreciated that these operations need not be performed in order.

Furthermore, it should be appreciated that not all of the operations need to be performed. The example operations may be performed in any order and in any combination. It should also be appreciated that the flow diagram is not all-inclusive, any other example embodiment described herein may also be applied to the flow diagram below, in any combination.

Example Operation 6

According to some of the example embodiments, the first radio node 400 is configured to receive 6 an information element indication a capability for determining the bandwidth of the second radio node 402 by calculating a correlation between a radio signal and a known signal. The digital circuitry 401 is configured to receive the information element indicating the capability for determining the bandwidth of the second radio node by calculation the correlation between the radio signal and the known signal.

It should be appreciated that example operation 6 is further discussed under at least the subheadings 'Overview of the example embodiments' and 'Capability'.

Example Operation 8

According to some of the example embodiments, the first radio node 400 is configured to send 8 and information element indicating a capability for determining the bandwidth of the second radio node 402 by calculating a correlation between a radio signal and a known signal. The digital circuitry 401 is configured to send the information element indicating the capability for determining the bandwidth of the second radio node by calculation the correlation between the radio signal and the known signal.

It should be appreciated that example operation 8 is further discussed under at least the subheadings 'Overview of the example embodiments' and 'Capability'.

Operation 10

The first radio node 400 is configured to receive 10, from the second radio node, a radio signal. The digital circuitry 401 is configured to receive, from the second radio node, the radio signal.

Operation 12

The first radio node 400 is further configured to determine 12 at least one known signal. The at least one known signal is transmittable on one or more known radio resources. Examples of radio resources are one or more of resource elements, resource blocks, time slots, subframe, radio frame, carrier frequency, subcarrier, channel bandwidth or its part, channelization code, CDMA codes, etc. The processing circuitry 403 is configured to determine the at least one known signal.

According to some of the example embodiments, the at least one known signal may be any one or more of CRS PRS, CSI-RS or DM-RS. It should be appreciated that operation 12 is further discussed under at least the subheadings 'Overview of the example embodiments', 'Obtaining bandwidth information in a wireless device', 'Obtaining and using bandwidth information in a radio network node' and 'Obtaining and using bandwidth information in a network node'.

Example Operation 14

According to some of the example embodiments, the determining 12 further comprises determining 14 the at least one known signal based on one or more pre-defined rules.

The processing circuitry 403 is configured to determine the at least one known signal based on one or more pre-defined rules.

It should be appreciated that the at least one known signal may be a plurality of known signals, where any number of the known signals comprise a pre-defined bandwidth. Examples of such pre-defined bandwidths are 1.4 MHz, 3 MHz, 5 MHz, 10 MHz, 15 MHz or 20 MHz in E-UTRAN. It should be appreciated that example operation 14 is further discussed under at least the subheadings 'Overview of the example embodiments', 'Obtaining bandwidth information in a wireless device', 'Obtaining and using bandwidth information in a radio network node' and 'Obtaining and using bandwidth information in a network node'.

Example Operation 16

According to some of the example embodiments, the determining 12 further comprises determining 16 the at least one known signal based on at least one signal characteristic of the received radio signal. The at least one signal characteristic comprises one or more of a signal type, a radio node identification, pseudo-random number generator parameters, associated time and/or frequency resources, and a number or identify of resource blocks comprised in a bandwidth of the radio signal. The processing circuitry 403 is configured to determine the at least one known signal based on at least one signal characteristic of the received radio signal.

It should be appreciated that example operation 16 is further discussed under at least the subheadings 'Overview of the example embodiments', 'Obtaining bandwidth information in a wireless device', 'Obtaining and using bandwidth information in a radio network node' and 'Obtaining and using bandwidth information in a network node'.

Operation 18

The first radio node 400 is further configured to calculate 18 a correction between the radio signal and the at least one known signal. The processing circuitry 403 is configure to calculate the correlation between the radio signal and the at least one known signal.

It should be appreciated that operation 18 is further discussed under at least the subheadings 'Overview of the example embodiments', 'Obtaining bandwidth information in a wireless device' as well as all subheadings within this heading, 'Obtaining and using bandwidth information in a radio network node' and 'Obtaining and using bandwidth information in a network node'.

Example Operation 20

According to some of the example embodiments, the at least one known signal is a plurality of known signals. In such example embodiments, the calculating 18 may further comprise calculating 20 a correlation between the radio signal and each of the plurality of know signals. The processing circuitry 403 is further configured to calculate the correlation between the radio signal and each of the plurality of known signals.

It should be appreciated that example operation 20 is further discussed under at least the subheadings 'Overview of the example embodiments', 'Obtaining bandwidth information in a wireless device', 'Obtaining and using bandwidth information in a radio network node' and 'Obtaining and using bandwidth information in a network node'.

Specifically, example operation 20 may further be described under the subheadings 'Bandwidth determination by correlation', 'Correlation over all possible bandwidths', 'Correlation over a selected set of bandwidths', and 'Correlation over differential bandwidths'.

Example Operation 22

According to some of the example embodiments, the at least one known signal is a plurality of known signals. In such example embodiments, the calculating 18 may further comprise calculating 22 an ordered correlation between the radio signal and at least a subset of the plurality of known signals. The processing circuitry 403 is configured to calculate the ordered correlation between the radio signal and at least the subset of the plurality of known signals.

It should be appreciated that the ordered correlation may be performed over a differential set of resource blocks. It should be appreciated that example operation 22 is further discussed under at least the subheadings 'Overview of the example embodiments', 'Obtaining bandwidth information in a wireless device', 'Obtaining and using bandwidth information in a radio network node' and 'Obtaining and using bandwidth information in a network node'.

Specifically, example operation 22 may further be described under the subheadings 'Bandwidth determination by correlation', 'Correlation over all possible bandwidths', 'Correlation over a selected set of bandwidths', and 'Correlation over differential bandwidths'.

Example Operation 24

According to some of the example embodiments, the calculating 22 may further comprise comparing 24 the ordered correlation with a threshold value. Thus, the calculating 22 of the ordered correlation may be performed until a respective ordered correlation surpasses the threshold value. The processing circuitry 403 is configured to compare the ordered correlation with a threshold value.

It should be appreciated that example operation 24 is further discussed under at least the subheadings 'Overview of the example embodiments', 'Obtaining bandwidth information in a wireless device', 'Obtaining and using bandwidth information in a radio network node' and 'Obtaining and using bandwidth information in a network node'.

Specifically, example operation 24 may further be described under the subheadings 'Bandwidth determination by correlation', 'Correlation over all possible bandwidths', 'Correlation over a selected set of bandwidths', and 'Correlation over differential bandwidths'.

Operation 26

The first radio node 400 is further configured to determine 26 a bandwidth of the second radio node based on the calculating 18. The processing circuitry 403 is configured to determine the bandwidth of the second radio node based on the calculating.

It should be appreciated that example operation 26 is further discussed under at least the subheadings 'Overview of the embodiments', 'Obtaining bandwidth information in a wireless device', 'Obtaining and using bandwidth information in a radio network node' and 'Obtaining and using bandwidth information in a network node'.

Specifically, operation 26 may further be described under the subheadings 'Bandwidth determination by correlation', 'Correlation over all possible bandwidths', 'Correlation over a selected set of bandwidths', and 'Correlation over differential bandwidths'.

Example Operation 28

According to some of the example embodiments, the calculating 20 and the determining 26 may further comprise determining 28 the bandwidth of the second radio node based on the known signal associated with a highest correlation value. The processing circuitry 403 is configured to determine the bandwidth of the second radio node based on the known signal associated with the highest correlation value.

It should be appreciated that example operation 28 is further discussed under at least the subheadings 'Overview of the example embodiments', 'Obtaining bandwidth information in a wireless device', 'Obtaining and using bandwidth information in a radio network node' and 'Obtaining and using bandwidth information in a network node'.

Specifically, example operation 28 may further be described under the subheadings 'Bandwidth determination by correlation', 'Correlation over all possible bandwidths', 'Correlation over a selected set of bandwidths', and 'Correlation over differential bandwidths'.

Example Operation 30

According to some of the example embodiments the calculating 22 and the determining 26 may further comprise determining 30 the bandwidth of the second radio node to be a bandwidth of a known signal associated with the ordered correlation which surpasses the threshold value. The processing circuitry 403 is configured to determine the bandwidth of the second radio node to be a bandwidth of a known signal associated with the ordered correlation which surpasses the threshold value.

It should be appreciated that example operation 30 is further discussed under at least the subheadings 'Overview of the example embodiments', 'Obtaining bandwidth information in a wireless device', 'Obtaining and using bandwidth information in a radio network node' and 'Obtaining and using bandwidth information in a network node'.

Specifically, example operation 30 may further be described under the subheadings 'Bandwidth determination by correlation', 'Correlation over all possible bandwidths', 'Correlation over a selected set of bandwidths', and 'Correlation over differential bandwidths'.

Example Operation 32

According to some of the example embodiments, the determining 26 further comprises determining 32 at least one other bandwidth based, at least in part, on the determined bandwidth of the second node 402. The processing circuitry 403 is configured to determine at least one other bandwidth based, as least in part, on the determined bandwidth of the second node 402.

It should be appreciated that example operation 32 is further discussed under at least the subheadings 'Overview of the example embodiments', 'Obtaining bandwidth information in a wireless device', 'Obtaining and using bandwidth information in a radio network node' and 'Obtaining and using bandwidth information in a network node'.

Specifically, example operation 32 may further be described under the subheading 'Determination of a second bandwidth'.

Example Operation 34

According to some of the example embodiments, the first radio node 400 may be further configured to send 34, to a wireless device and/or network node, the determined bandwidth. The digital circuitry 401 is configured to send, to the wireless device and/or network node, the determined bandwidth.

It should be appreciated that example operation 34 is further discussed under at least the subheadings 'Overview of the example embodiments', 'Obtaining bandwidth information in a wireless device', 'Obtaining and using bandwidth information in a radio network node', 'Obtaining and using bandwidth information in a network node' and 'Example uses of the determined bandwidth'.

Example Operation 36

According to some of the example embodiments, the first radio node 400 may be further configured to utilize the determined bandwidth of the second radio node 402. The utilization may comprise any one or more of adapting receiver parameter(s) and/or a receiver type, verifying a bandwidth of the second radio node, determining an activity of a signal transmitted by the second radio node, network planning and optimization, minimization of drive test, positioning, radio resource management, inter-cell interference coordination, handling interference from an interfering cell, mitigating interference from an interfering cell, neighbour cell relation establishment, assistance data creation, wireless device measurement configurations, performing a radio measurement, performing radio link monitoring (RLM), and aggregate indication indicating a bandwidth of a plurality of cells. The processing circuitry 403 is configured to utilized the determined bandwidth of the second radio node 402.

It should be appreciated that example operation 36 is further discussed under at least the subheadings 'Overview of the example embodiments', 'Obtaining bandwidth information in a wireless device', 'Obtaining and using bandwidth information in a radio network node', 'Obtaining and using bandwidth information in a network node' and 'Example uses of the determined bandwidth'.

It should be noted that although terminology from 3GPP LTE has been used herein to explain the example embodiments, this should not be seen as limiting the scope of the example embodiments to only the aforementioned system. Other wireless systems, comprising HSPA, WCDMA, WiMax, UMB, WiFi and GSM, may also benefit from the example embodiments disclosed herein.

The description of the example embodiments provided herein have been presented for purposes of illustration. The description is not intended to be exhaustive or to limit example embodiments to the precise form disclosed, and modifications and variations are possible in light of the above teachings or may be acquired from practice of various alternatives to the provided embodiments. The examples discussed herein were chosen and described in order to explain the principles and the nature of various example embodiments and its practical application to enable one skilled in the art to utilize the example embodiments in various manners and with various modifications as are suited to the particular use contemplated. The features of the embodiments described herein may be combined in all possible combinations of methods, apparatuses, modules, systems, and computer program products. It should be appreciated that the example embodiments presented herein may be practiced in any combination with each other.

It should be noted that the word "comprising" does not necessarily exclude the presence of other elements or steps than those listed and the words "a" or "an" preceding an element do not exclude the presence of a plurality of such elements. It should further be noted that any reference signs do not limit the scope of the claims, that the example embodiments may be implemented at least in part by means of both hardware and software, and that several "means", "units" or "devices" may be represented by the same item of hardware.

Also note that terminology such as user equipment should be considered as non-limiting. A wireless terminal or user equipment (UE) as the term is used herein, is to be broadly interpreted to comprise a radiotelephone having ability for Internet/intranet access, web browser, organizer, calendar, a camera, e.g., video and/or still image camera, a sound recorder, e.g., a microphone, and/or global positioning system (GPS) receiver; a personal communications system (PCS) user equipment that may combine a cellular radiotelephone with data processing; a personal digital assistant (PDA) that can comprise a radiotelephone or wireless communication system; a laptop; a camera, e.g., video and/or still image camera, having communication ability; and any other computation or communication device capable of transceiving, such as a personal computer, a home entertainment system, a television, etc. It should be appreciated that the term user equipment may also comprise any number of connected devices, wireless terminals or machine-to-machine devices.

It should further be appreciated that the term dual connectivity should not be limited to a user equipment or wireless terminal being connected to only two base stations. In dual connectivity a wireless terminal may be connected to any number of base stations.

The various example embodiments described herein are described in the general context of method steps or processes, which may be implemented in one aspect by a computer program product, embodied in a computer-readable medium, comprising computer-executable instructions, such as program code, executed by computers in networked environments. A computer-readable medium may comprise removable and non-removable storage devices comprising, but not limited to, Read Only Memory (ROM), Random Access Memory (RAM), compact discs (CDs), digital versatile discs (DVD), etc. Generally, program modules may comprise routines, programs, objects, components, data structures, etc. that perform particular tasks or implement particular abstract data types. Computer-executable instructions, associated data structures, and program modules represent examples of program code for executing steps of the methods disclosed herein. The particular sequence of such executable instructions or associated data structures represents examples of corresponding acts for implementing the functions described in such steps or processes.

In the drawings and specification, there have been disclosed exemplary embodiments. However, many variations and modifications can be made to these embodiments. Accordingly, although specific terms are employed, they are used in a generic and descriptive sense only and not for purposes of limitation.

The invention claimed is:

1. A method, in a first radio node, for determining a bandwidth of a second radio node, the first and second radio nodes being configured for use in a communications network, the method comprising:
   receiving, from the second radio node, a radio signal;
   determining a plurality of known signals, said plurality of known signals being transmittable on one or more known radio resources, wherein said plurality of known signals is ranked according to a bandwidth of each respective known signal;
   calculating a correlation between the radio signal and each of one or more of the plurality of known signals, wherein the calculating of the correlation comprises calculating an ordered correlation between the radio signal and at least a subset of said plurality of known signals and comparing said ordered correlation with a threshold value, wherein said calculating the ordered correlation is performed until a respective ordered correlation surpasses said threshold value; and
   determining a bandwidth of the second radio node based on the calculating, wherein said determining the bandwidth further comprises determining the bandwidth of the second radio node to be a bandwidth of the known signal associated with the ordered correlation that surpasses said threshold value; and
   utilizing said determined bandwidth of the second radio node for any one or more of adapting one or more receiver parameters or adapting a receiver type or adapting both one or more receiver parameters and receiver type.

2. The method of claim 1, wherein the determining of the plurality of known signals further comprises determining said plurality of known signals based on one or more predefined rules.

3. The method of claim 1, wherein the determining of the plurality of known signals further comprises determining said plurality of known signals based on at least one signal characteristic of the received radio signal, said at least one signal characteristic comprising one or more of a signal type, a radio node identification, pseudo-random number generator parameters, associated time resources or frequency resources or both, and a number or identity of resource blocks comprised in a bandwidth of the radio signal.

4. The method of claim 1, wherein said determining further comprises determining the bandwidth of the second radio node based on the known signal associated with a highest correlation value.

5. The method of claim 1, wherein the bandwidth of each respective known signal is pre-defined, wherein said pre-defined bandwidths are 1.4 MHz, 3 MHz, 5 MHz, 10 MHz, 15 MHz or 20 MHz.

6. The method of claim 1, wherein calculating of the ordered correlation is performed over a differential set of resource blocks.

7. The method of claim 1, wherein the determining the bandwidth of the second radio node further comprises determining at least one other bandwidth based, at least in part, on the determined bandwidth of the second node.

8. The method of claim 1, further comprising receiving or sending or both receiving and sending an information element indicating a capability for determining the bandwidth of the second radio node by calculating a correlation between a radio signal and a known signal.

9. The method of claim 1, further comprising sending, to a wireless device or to a network node or to both a wireless device and a network node, said determined bandwidth.

10. The method of claim 1, further comprising utilizing said determined bandwidth of the second radio node for any one or more of verifying a bandwidth of a second radio node, determining an activity of a signal transmitted by the second node, network planning and optimization, minimization of drive test, positioning, radio resource management, inter-cell interference coordination, handling interference from an interfering cell, mitigating interference from an interfering cell, neighbour cell relation establishment, assistance data creation, wireless device measurement configurations, performing a radio measurement, performing radio link monitoring, and aggregate indication indicating a bandwidth of a plurality of cells.

11. The method of claim 1, wherein the plurality of known signals comprise any one or more of Cell-specific Reference Signals (CRS) Positioning Reference Signals (PRS) Channel State Information-Reference Signal (CSI-RS) or Demodulation Reference Signals (DM-RS).

12. A first radio node for determining a bandwidth of a second radio node, the first and second radio nodes being configured for use in a communications network, the first radio node comprising:
   radio circuitry configured to receive, from the second radio node, a radio signal;
   processing circuitry configured to determine a plurality of known signals, said plurality of known signals being transmittable on one or more known radio resources, wherein said plurality of known signals is ranked according to a bandwidth of each respective known signal;

said processing circuitry being further configured to calculate a correlation between the radio signal and each of one or more of the plurality of known signals, wherein the calculating of the correlation comprises calculating an ordered correlation between the radio signal and at least a subset of said plurality of known signals and comparing said ordered correlation with a threshold value, wherein said calculating the ordered correlation is performed until a respective ordered correlation surpasses said threshold value; and said processing circuitry being further configured to determine a bandwidth of the second radio node based on the calculated correlation, wherein said determining the bandwidth further comprises determining the bandwidth of the second radio node to be a bandwidth of the known signal associated with the ordered correlation that surpasses said threshold value; and said processing circuitry being still further configured to utilize said determined bandwidth of the second radio node for any one or more of adapting one or more receiver parameters or adapting a receiver type or adapting both one or more receiver parameters and receiver type.

13. The first radio node of claim 12, wherein the processing circuitry is further configured to determine said plurality of known signals based on one or more predefined rules.

14. The first radio node of claim 12, wherein the processing circuitry is further configured to determine said plurality of known signals based on at least one signal characteristic of the received radio signal, said at least one signal characteristic comprising one or more of a signal type, a radio node identification, pseudo-random number generator parameters, associated time resources or frequency resources or both, and a number or identity of resource blocks comprised in a bandwidth of the radio signal.

15. The first radio node of claim 12, wherein processing circuitry is further configured to determine the bandwidth of the second radio node based on the known signal associated with a highest correlation value.

16. The method of claim 12, wherein the bandwidth of each respective known signal is pre-defined, wherein said pre-defined bandwidths are 1.4 MHz, 3 MHz, 5 MHz, 10 MHz, 15 MHz or 20 MHz.

17. The method of claim 12, wherein calculating of the ordered correlation is performed over a differential set of resource blocks.

18. The first radio node of claim 12, wherein the processing circuitry is further configured to determine at least one other bandwidth based, at least in part, on the determined bandwidth of the second node.

19. The first radio node of claim 12, wherein said radio circuitry is further configured to send or receive or both send and receive an information element indicating a capability for determining the bandwidth of the second radio node by calculating a correlation between a radio signal and a known signal.

20. The first radio node of claim 12, wherein said radio circuitry is further configured to send, to a wireless device or to a network node or to both a wireless device and a network node, said determined bandwidth.

21. The first radio node of claim 12, wherein the processing circuitry is further configured to utilize said determined bandwidth of the second radio node for any one or more of verifying a bandwidth of a second radio node, determining an activity of a signal transmitted by the second node, network planning and optimization, minimization of drive test, positioning, radio resource management, inter-cell interference coordination, handling interference from an interfering cell, mitigating interference from an interfering cell, neighbour cell relation establishment, assistance data creation, wireless device measurement configurations, performing a radio measurement, performing radio link monitoring, and aggregate indication indicating a bandwidth of a plurality of cells.

22. The first radio node of claim 12, wherein the plurality of known signals comprise any one or more of Cell-specific Reference Signals (CRS) Positioning Reference Signals (PRS) Channel State Information-Reference Signal (CSI-RS) or Demodulation Reference Signals (DM-RS).

23. The first radio node of claim 12, wherein the first radio node is a wireless device, a base station, a remote radio unit, a remote radio head, access point, or a location measurement unit.

* * * * *